(12) United States Patent
Berthier et al.

(10) Patent No.: US 9,987,629 B2
(45) Date of Patent: Jun. 5, 2018

(54) METHODS, SYSTEMS, AND DEVICES RELATING TO OPEN MICROFLUIDIC CHANNELS

(71) Applicant: Tasso, Inc., Madison, WI (US)

(72) Inventors: Erwin Berthier, Madison, WI (US); Ben Casavant, Seattle, WA (US); Ben Moga, Houston, TX (US)

(73) Assignee: Tasso, Inc., Seattle, WA (US)

( * ) Notice: Subject to any disclaimer, the term of this patent is extended or adjusted under 35 U.S.C. 154(b) by 0 days. days.

(21) Appl. No.: 14/932,485

(22) Filed: Nov. 4, 2015

(65) Prior Publication Data
US 2016/0051981 A1 Feb. 25, 2016

Related U.S. Application Data

(63) Continuation of application No. 13/949,108, filed on Jul. 23, 2013, now Pat. No. 9,289,763.
(Continued)

(51) Int. Cl.
*B01L 3/00* (2006.01)
*A61B 5/15* (2006.01)
*A61B 5/151* (2006.01)

(52) U.S. Cl.
CPC ........ *B01L 3/50273* (2013.01); *A61B 5/1411* (2013.01); *A61B 5/150022* (2013.01);
(Continued)

(58) Field of Classification Search
CPC ...... B01L 3/50273; B01L 3/00; A61B 5/1411; A61B 5/150022; A61B 5/150061; A61B 5/150221
(Continued)

(56) References Cited

U.S. PATENT DOCUMENTS

| 5,035,865 A | 7/1991 | Inaba et al. |
| 5,145,565 A | 9/1992 | Kater et al. |

(Continued)

OTHER PUBLICATIONS

Atencia J, Beebe DJ, "Controlled Microfluidic Interfaces", Sep. 29, 2005, pp. 648-655, vol. 437, No. 7059, Publisher: Nature.
(Continued)

*Primary Examiner* — Brian J. Sines
(74) *Attorney, Agent, or Firm* — Davis, Brown, Koehn, Shors & Roberts, P.C.; Matthew Warner-Blankenship

(57) ABSTRACT

The various embodiments described herein relate to fabricating and using open microfluidic networks according to methods, systems, and devices that can be used in applications ranging from home-testing, diagnosis, and research laboratories. Open microfluidic networks allow the input, handling, and extraction of fluids or components of the fluid into or out of the open microfluidic network. Fluids can be inserted into an open microfluidic channel by using open sections of the open microfluidic network. Passive valves can be created in the microfluidic network, allowing the creation of logic circuits and conditional flow and volume valves. The fluid can be presented via the microfluidic network to diagnostic and analysis components. Fluids and components of the fluid can be extracted from the open microfluidic network via functional open sections that are easily interfaced with other microfluidic networks or common laboratory tools.

9 Claims, 24 Drawing Sheets

Related U.S. Application Data

(60) Provisional application No. 61/674,415, filed on Jul. 23, 2012.

(52) U.S. Cl.
CPC .... *A61B 5/150061* (2013.01); *A61B 5/15105* (2013.01); *A61B 5/15146* (2013.01); *A61B 5/150221* (2013.01); *A61B 5/150343* (2013.01); *A61B 5/150419* (2013.01); *A61B 5/150969* (2013.01); *A61B 5/150984* (2013.01); *B01L 3/5027* (2013.01); *B01L 3/502723* (2013.01); *B01L 3/502738* (2013.01); *B01L 2200/0621* (2013.01); *B01L 2200/0684* (2013.01); *B01L 2300/0672* (2013.01); *B01L 2300/0816* (2013.01); *B01L 2300/0861* (2013.01); *B01L 2300/0867* (2013.01); *B01L 2300/161* (2013.01); *B01L 2400/0406* (2013.01); *B01L 2400/0688* (2013.01); *B01L 2400/086* (2013.01)

(58) Field of Classification Search
USPC .............. 422/507, 502, 503, 504, 547, 549; 436/43, 180
See application file for complete search history.

(56) References Cited

U.S. PATENT DOCUMENTS

| | | |
|---|---|---|
| 5,320,607 A | 6/1994 | Ishibashi |
| 6,152,942 A | 11/2000 | Brenneman et al. |
| 6,364,890 B1 | 4/2002 | Lum et al. |
| 6,605,048 B1 | 8/2003 | Levin et al. |
| 6,660,018 B2 | 12/2003 | Lum et al. |
| 6,856,821 B2 | 2/2005 | Johnson |
| 7,288,073 B2 | 10/2007 | Effenhauser et al. |
| 7,374,545 B2 | 5/2008 | Alroy et al. |
| 7,666,149 B2 | 2/2010 | Simons et al. |
| 7,803,123 B2 | 9/2010 | Perez et al. |
| 8,162,854 B2 | 4/2012 | Calasso et al. |
| 8,696,596 B2 | 4/2014 | Douglas et al. |
| 8,728,411 B2 | 5/2014 | Beebe et al. |
| 9,033,898 B2 | 5/2015 | Chickering, III et al. |
| 2002/0097632 A1 | 7/2002 | Kellogg et al. |
| 2003/0018282 A1 | 1/2003 | Effenhauser et al. |
| 2003/0028125 A1 | 2/2003 | Yuzhakov et al. |
| 2004/0243105 A1 | 12/2004 | Swan et al. |
| 2006/0171855 A1 | 8/2006 | Yin et al. |
| 2007/0212266 A1 | 9/2007 | Johnston et al. |
| 2007/0260193 A1 | 11/2007 | Chin et al. |
| 2008/0028821 A1 | 2/2008 | Horiike et al. |
| 2009/0187118 A1 | 7/2009 | Kim et al. |
| 2009/0192486 A1* | 7/2009 | Wilmot ............... A61M 5/2033 604/506 |
| 2010/0256524 A1 | 10/2010 | Levinson et al. |
| 2010/0326826 A1 | 12/2010 | Harrison et al. |
| 2011/0077553 A1 | 3/2011 | Alroy |
| 2011/0257498 A1 | 10/2011 | Amano et al. |
| 2011/0312773 A1 | 12/2011 | Silverbrook et al. |
| 2012/0010529 A1* | 1/2012 | Chickering, III .... A61B 5/1411 600/576 |
| 2012/0048931 A1 | 3/2012 | Delamarche et al. |
| 2012/0088249 A1 | 4/2012 | Jovanovich et al. |
| 2013/0211289 A1 | 8/2013 | Moga et al. |
| 2014/0038306 A1 | 2/2014 | Berthier et al. |
| 2014/0042094 A1 | 2/2014 | Montagu et al. |
| 2014/0190894 A1 | 7/2014 | Beebe et al. |
| 2014/0273056 A1 | 9/2014 | Beebe et al. |

OTHER PUBLICATIONS

Berry SM, Alarid ET, Beebe DJ, "One-step purification of nucleic acid for gene expression analysis via Immiscible Filtration Assisted by Surface Tension(IFAST)", Jan. 4, 2011, pp. 1747-1753, vol. 11, No. 10, Publisher: Lab Chip.

David Chunningham, Timothy Henning, Eric Shain, Douglas Young Jurgen Hanning, Eric Barua, Raphael Lee, "Blood extration from lancet wounds using vacuum combined with skin stretching", Nov. 9, 2001, pp. 1089-1096, vol. 92, No. 3, Publisher: J Appl Physiol.

H Fruhstorfer, H Lange, "Capillary blood sampling: how much pain is necessary? Part 3: Pricking the finger can be less painful", Feb. 1, 1995, pp. 253-254, vol. 12, No. 6, Publisher: Practical Diabetes International.

H Fruhstorfer, T Muller, "Capillary blood sampling: how much pain is necessary? Part 1: Comparison of existing finger stick devices", Feb. 1, 1995, pp. 72-74, vol. 12, No. 2, Publisher: Practical Diabetes Internationa.

H Fruhstorfer, T Muller, E Scheer, "Capillary blood sampling: how much pain is necessary? Part 2: Relation between penetration depth and puncture pain", Feb. 1, 1995, pp. 184-185, vol. 12, No. 4, Publisher: Practical Diabetes Internationa.

Heinrich Fruhstorfer, Gunther Schmelzeisen-Redeker, Thomas Weiss, "Capilary Blood Sampling: relation between lancet diameter, lancing pain and blood volume", 1999, pp. 283-286, vol. 3, No. 3, Publisher: European Journal of Pain.

H Fruhstorfer, K Selzer, O Selbman, "Capillary blood sampling: how much pain is necessary? Part 4: Comparison of lancets for automatic lancing devices", Jul. 24, 1995, pp. 58-60, vol. 13, No. 2, Publisher: Practical Diabetes Internationa.

Heinrich Fruhstorfer, "Cpillary Blood Sampling: the pain of single-use lancing devices", 2000, pp. 301-305, vol. 4, No. 3, Publisher: European Journal of Pain.

Chia-Hsien Hsu, Chihchen Chen, Albert Folch, "Microcanals for micropipette access to single cells in microfluidic environments", Jul. 23, 2004, pp. 420-424, vol. 4, No. 5, Publisher: Lab Chip.

J. Berthier, F. Loe-Mie, V.-M. Tran, S Schoumacker, F. Mittler, G. Marchand, N. Sarrut, "On the Pinning of interfaces on micropillar edges", Jun. 3, 2009, pp. 296-303, vol. 338, No. 1, Publisher: J Colloid Interface Sci.

Sung Hoon Lee, Austen James Heinz, Sunghwan Shin, Young-Gyun Jung, Sung-Eun Choi, Wook Park, Jung-Hye Roe, Sunghoon Kwon, "Capillary Based Patterning of Cellular communities in the Laterally Open Channels", 2010, pp. 2900-2906, vol. 82, No. 7, Publisher: Anal Chem.

"Open Microfluidic and Nanofluidic systems", Feb. 15, 2005, pp. 1848-1852, vol. 102, Publisher: PNAS.

Nuno M. Oliveira, Ana I. Neto, Wenlong Song, Joao F. Mano, "Two-Dimensional Open Microfluidic Devices by Tuning the Wettability on Patterned Superhydrophobic Polymeric Surface", Aug. 6, 2010, vol. 3:085205, Publisher: Appl Phys Express.

Jessica Olofsson, Johan Pihl, Jon Sinclair, Eskil Sahlin, Mattias Karlsson, Owe Orwar, "A Microfluidics Approach to the Problem of Creating Separate Solution Environments Accessible from Macroscopic Volumes", 2004, pp. 4968-4976, vol. 76, No. 17, Publisher: Anal Chem.

Ralf Seemann, Martin Brinkmann, Edward J. Kramer, Frederick F. Lange, Reinhard Lipowsky, "Wetting morphologies at microstructured surfaces", Dec. 16, 2004, pp. 1848-1852, vol. 102, No. 6, Publisher: Proc Natl Acad Sci USA.

Bin Zhao, Jeffrey S. Moore, David J. Beebe, "Surface-Directed Liquid Flow Inside Microchannels", 2001, pp. 1023-1026, vol. 291, No. 5506, Publisher: Science.

* cited by examiner

20

21

21a 23a  24a

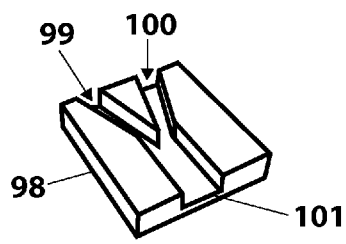
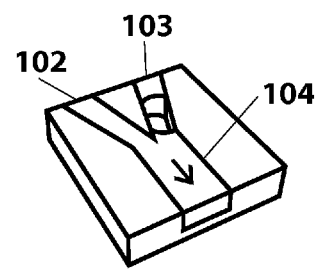
Figure 10A
Figure 10B
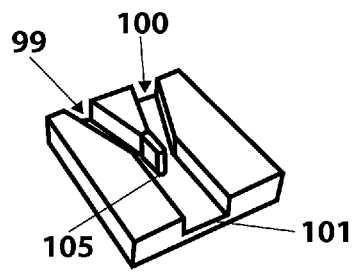
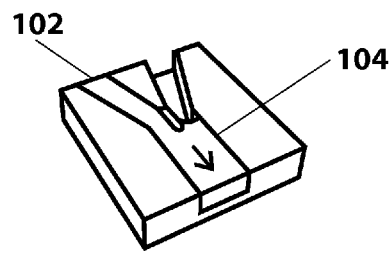
Figure 10C
Figure 10D

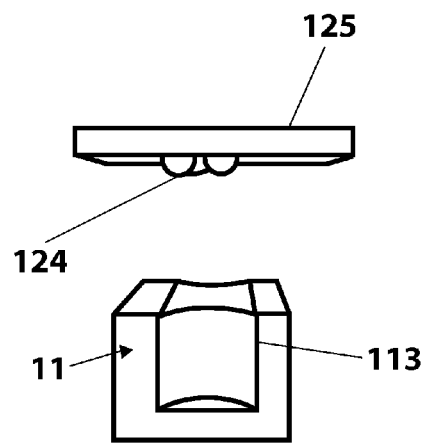 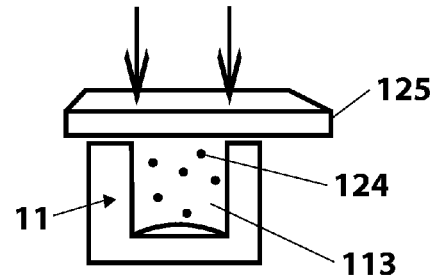
Figure 14A          Figure 14B
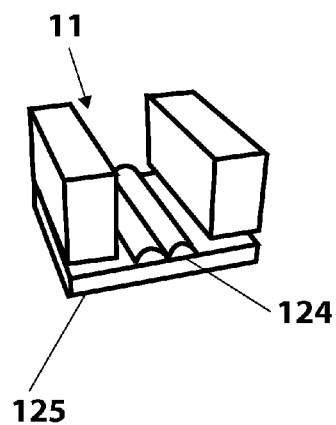 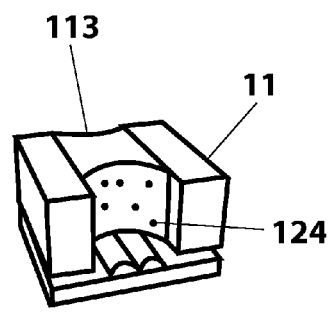
Figure 14C          Figure 14D

METHODS, SYSTEMS, AND DEVICES RELATING TO OPEN MICROFLUIDIC CHANNELS

CROSS REFERENCE TO RELATED APPLICATIONS

This application is a continuation of U.S. application Ser. No. 13/949,108, filed Jul. 23, 2013, entitled "Methods, Systems, and Devices Relating to Open Microfluidic Channels," which issued as U.S. Pat. No. 9,289,763 on Mar. 22, 2016 and claimed priority from U.S. Provisional Application 61/674,415, filed Jul. 23, 2012, and entitled "Methods, Systems, and Devices Relating to Open Microfluidic Channels," which are hereby incorporated herein by reference in their entirety.

TECHNICAL FIELD

The present technology relates to various methods, systems, and devices regarding fluid handling for medical devices, and in particular, interfacing bodily fluids with a microfluidic network and the subsequent handling of the fluid in order to direct it towards diagnostic sensing or biomarker analysis components.

BACKGROUND

An open microchannel is defined as a microfluidic channel whose cross-section is composed of solid walls as well as at least one section with open liquid-air interface. Open microchannels present advantageous properties linked to their reliability, function, and manufacturability. Open microchannels solve a problem related to air bubbles, as the gas can escape through the open face of the channel, thus creating a device that is more reliable in comparison to traditional closed channel setups. However, prior to the inventions described herein, flow in open microfluidic channels was not well understood, and the few existing methods demonstrated until now have had limited functionality, namely transporting fluid for a short distance in a straight line, as described in the filed patent Ser. No. 11/470,021 and 09/943,080. A second problem in existing technology relating to open microfluidic channels was the lack of ability to control the flow of fluid, thus preventing the creation of advanced fluid handling platforms designed entirely or in large part based on that technology. Thirdly, there was, prior to the inventions described herein, a lack of tools allowing for the insertion of fluid into, or removal of fluid from, the open channel. All of the known methods relied on dipping a single device into the liquid of interest in order to sample a small amount, rather than having the ability to create networks in which fluid can be inserted at precise locations and at different times. Further, no known method prior to the inventions described herein provides for the removal of fluid from these channels. Thus, there is a need in the art for improved open microfluidic channels and related systems, devices, and methods.

BRIEF SUMMARY

The disclosed apparatus, systems and methods relate to the benefits in the manufacturing of shallow open microchannels, as this can be performed in one single molding or embossing step as it does not require bonding to enclose the channel, enabling large scale manufacturing of complex networks at low costs. These advantages make open microchannel networks particularly well suited for disposable diagnostic devices for which fluids require precise handling with low manufacturing costs. This document describes a set of methods and embodiments that facilitate new methods for handling fluid or bodily samples and enable the interfacing with microfluidic networks in new ways. The preferred embodiment of the approaches described is for use in medical devices, at-home diagnostic devices, and laboratory analysis platforms.

The ability to create flow in open microfluidic channels is a required condition for creating functional open microfluidic networks. As open microfluidic channels contain open liquid-air interfaces, pressure sources are not the preferred method to drive fluid flow; rather spontaneous capillary flow offers a reliable, scalable driving force for fluid flow. The use of capillary-driven flow to manipulate fluids in complex open microfluidic networks is a novel feature previously unused in open microfluidic channels. In order to insure that spontaneous capillary flow (SCF) occur in a channel containing any number of open liquid-air interfaces in its cross-section, an analysis of capillary force was developed, to define a design guideline ensuring that the capillary force provided by the walls of the microfluidic channel overcomes the resistance created by the open sections of the microfluidic channel. The result of the analysis is written in a SCF relation stating that the ratio of the free perimeter ($p_f$), defined by the length of the cross-section open to air or another medium, and the wetted perimeter ($p_w$), defined by the length of the cross-section made up of solid hydrophilic material must be less than the cosine of the contact angle ($\theta$) of the fluid with the channel walls. When the SCF relation is satisfied, the channel will drive the flow through the microfluidic network by capillary forces. Importantly, the SCF relation extends to most channel configurations containing open liquid-air and wetted sections. Further, the open liquid-air sections do not have to be continuous or contiguous. Thus the SCF relation still holds for complex channel geometries containing open "windows" on the channel (e.g. a circular aperture in the wall of a channel) as well channels containing multiple open liquid-air interfaces at the same point in the channel (e.g. a fluid completely suspended between two rails in a channel devoid of ceiling and floor). Open microfluidic channels verifying the SCF relation also have the benefit of not being constrained to rectangular cross-sections. The SCF relation can be written in equation (1):

$$p_f/p_w < \cos(\theta) \quad (1)$$

Equation (1) represents the fundamental physical background for the development of the building blocks for the handling of fluids in open microfluidic networks described in the patent following. Importantly, open microfluidic methods eliminate the problem inherent in microfluidics of bubble formation being catastrophic within a microchannel, and enable simplified manufacturing due to no required bonding to seal the channel. We have developed fluid manipulation techniques based on open channel concepts, which are the building blocks to create a microfluidic fluid handling network amenable to human bodily fluid collection and analysis. The two aspects covered by this invention pertain to (1) handling fluid into and out of the microfluidic network and (2) handling techniques within the microfluidic network. The development of an analytical model for describing conditions of flow in open microfluidic channels has lead to the establishment of an equation detailing the geometrical conditions for flow in open microfluidic networks and precise design guidelines that enable a dramatic expansion of the functionalities of open microfluidic systems. One of the enabling aspects of such a development is the ability to flow fluids in shallow open microfluidic grooves, open microfluidic grooves with non-rectangular cross-sections, non-planar and angled open microfluidic grooves, as well as open microfluidic systems with more than one open interface (e.g. no channel ceiling nor floor).

The open microfluidic handling methods developed enable novel mechanisms to bring fluid into and out of the microfluidic network, and can incorporate methods including extracting fluid from a pool or droplet on a surface, such as human skin, from a reservoir, or from another open microfluidic channel. The design rules developed, made explicit by the SCF relation described in equation (1), allow the creation of open capillary networks amenable to capturing blood pooling on the surface of the skin (as is the case for many diagnostic applications) and transferring it into an open fluidic network. Additionally, it enables the design of open interconnection features allowing the transfer of fluids from one open microfluidic network to another. The possibility of extracting and exchanging fluids from one open microfluidic channel to another enables the use of open microfluidic devices to create complex assays by assembling pre-fabricated standard building blocks or by leveraging 3D geometries simply by placing one open microfluidic network on top of another, while allowing fluidic contacts from one network to the other. Importantly, these methods can operate regardless of air bubble formation, as there is at least one open liquid-air interface present in the channel, such as in a channel with a U-shaped cross-section containing no ceiling atop the microfluidic channel. Further, open microfluidic networks can leverage the open interface area to insert immiscible fluids or gases to sever the fluid present in the channel in two sections. The ability of separating fluids in sections allows the creation of user actuated open microfluidic valves that are the basis of advanced control over fluid flows in open microfluidic networks.

Shallow open microfluidic methods also enable the creation of fluidic networks that can be readily interfaces with traditional pipetting systems in order to perform robotic interfacing with the microfluidic network. The design guidelines developed also enable the creation of microfluidic grooves that have the ability to drive the flow of fluid using only a subset of the walls of the channel and not the totality of the walls of the channel, such that the flow can be propelled around edges that would usually cause pinning. The flow pas pinning edges and lines further enables the creation of non-planar channels that flow around concave and convex angles, or onto a new plane branching off of the main microfluidic channel. The design rules developed also allow the capillary flow of a fluid over heterogeneous patches on the wall or floor of the microfluidic groove. Such patches can include absorbent pads for capture of blood, reaction sites for detection of blood analytes, translucent materials for optical analysis of the blood, or open apertures for physical access to the blood in the microfluidic groove. Particularly, open apertures can be used to add or remove substance from the channel, connected to a substance-specific removal area (e.g. an organic solvent for chemical extraction, antibody-laden hydrogel for detection, magnet for magnetic bead removal), or a large, set volume opening for contact with another open fluid or extraction method.

The other important aspects of the open microfluidic handling methods pertain to handling techniques of fluid within the microfluidic network. Because a specific set of design constraints can be used to create flow within a microfluidic network, they can also be leveraged to create unique functionality within the open microfluidic network that otherwise could not be achieved with closed microfluidic systems or other open microfluidic systems. The first general method enabled by open microfluidic systems pertain to the unique ability to pin a fluid in a channel devoid of a ceiling. The design guideline provides precise geometrical rules for describing the conditions of flow in an open microfluidic channel, and by corollary the conditions for which flow cannot occur in an open microfluidic groove. Thus a channel can be designed such that at a certain location the conditions for flow are conditionally met based on a user-actuated system. The second general set of methods pertains to manipulating the channel walls or creating unique flow environments within the open microfluidic network. These methods can include flowing the fluid over an aperture in the floor of the channel such that the fluid does not pin at this surface, placing a dried substance on the walls of the channel such that a fluid flows therein and incorporates the substance into the fluid, creating a mechanism for capillary pulling of fluid from one of the open channel to the other, directing fluid to multiple planes at any angle, or a mechanism for allowing asynchronous fluids from various channels to incorporate into a larger channel or chamber without air bubble formation or dissipation. The latter method is enabled by the open microfluidic environment as two fluids present in the channel at any location will not provoke the entrapment of an air bubble, as gas will be able to escape through the open liquid-air section, thus the two fluids coming from either input channel in the branching area can merge without risking catastrophic failure of the microfluidic system. Additionally, the open microfluidic approach enables the connection of multiple networks together without risking the entrapment of air bubbles that prevent further use of the microfluidic network.

All of these methods can be used to create complex fluidic networks that could be useful in a variety of applications, either in simple point-of-care devices (incorporating a dried or lyophilized sample into the channel, combining multiple channels to a central location) or for more complex fluid networks, which can be interfaced with liquid handling systems. Open networks are enabling for the reliability of these complex fluid networks, and further enhance the ability to fabricate channels in high throughput, as no bonding is necessary to complete device fabrication.

Certain examples shall now be described.

In Example 1, a microfluidic device comprises a first microscaled channel configured to allow flow of fluids by capillary action, wherein the channel has at least one portion of the channel comprising a first cross-section. The first cross-section comprises a wetted surface comprising hydrophilic material and a free interface comprising an open air-liquid interface. The wetted surface contacts fluid flowing through the channel. The ratio of a cross-sectional length of the free interface and a cross-sectional length of the wetted surface is less than the cosine of the contact angle, thereby permitting spontaneous capillary flow.

Example 2 relates to the microfluidic device according to Example 1, wherein the first cross-section further comprises at least two wetted surfaces, and an interface with a high contact angle, a hydrophobic area, or a second free liquid-air interface.

Example 3 relates to the microfluidic device according to Example 2, wherein the first cross-section comprises a rectangular or trapezoidal shape, wherein the free interface comprises a first free interface defined in a top portion of the first cross-section and a second free interface defined in a bottom portion of the first cross-section.

Example 4 relates to the microfluidic device according to Example 1, wherein the free interface is defined in a bottom portion of the device such that the free interface can be brought into contact with a volume of fluid pooling on a surface, thereby causing capture of at least a portion of the volume and flow of the volume into the groove.

Example 5 relates to the microfluidic device according to Example 1, wherein the first microscale channel further comprises a second free interface comprising an open air-liquid interface or an insert of optically transparent material, wherein the first channel is configured to allow flow of fluid over the second free interface, and wherein the second free interface defines a light path configured to allow light to strike the fluid in the groove in order to perform a fluorescence or spectrometry analysis of the fluid.

Example 6 relates to the microfluidic device according to Example 1, wherein the open air-liquid interface is configured to provide access for the removal of a fluid sample from the channel or any component of that fluid sample.

Example 7 relates to the microfluidic device according to Example 6, wherein the open air-liquid interface is configured to receive a second capillary channel, thereby allowing the fluid flow into a second fluidic network.

Example 8 relates to the microfluidic device according to Example 1, wherein the first channel further comprises a second cross-section that comprises a first configuration and a second configuration. The first configuration has a ratio of a cross-sectional length of a free interface and a cross-sectional length of a wetted surface that is greater than the cosine of the contact angle, thereby preventing spontaneous capillary flow. The second configuration has a ratio of the cross-sectional length of the free interface and a cross-sectional length of the wetted surface that is less than the cosine of the contact angle.

Example 9 relates to the microfluidic device according to Example 8, further comprising a conversion mechanism configured to convert the second cross-section from the first configuration to the second configuration and from the second configuration to the first configuration.

Example 10 relates to the microfluidic device according to Example 9, wherein the conversion mechanism comprises a presence or absence of an immiscible fluid over at least part of the open air-liquid interface of the second cross-section, such that the immiscible fluid constitutes a portion of the wetted surface.

Example 11 relates to the microfluidic device according to Example 11, wherein the conversion mechanism comprises a solid material configured to move between a position non-adjacent to the first channel and a position coupled with the first channel, such that the material constitutes a portion of the wetted surface.

Example 12 relates to the microfluidic device according to Example 9, wherein the conversion mechanism comprises movement of the walls of the first channel between the first configuration and the second configuration.

Example 13 relates to the microfluidic device according to Example 1, wherein the channel comprises a material configured to remove at least a portion of the fluid.

Example 14 relates to the microfluidic device according to Example 13, wherein the channel comprises an aperture defined in the channel, wherein the aperture provides fluid access to an external environment.

Example 15 relates to the microfluidic device according to Example 13, wherein the material comprises a hydrogel, paper, or another liquid-absorbent material.

Example 16 relates to the microfluidic device according to Example 13, wherein the material comprises an inorganic phase, an organic solvent, an antibody-laden hydrogel or another analyte-extracting material.

Example 17 relates to the microfluidic device according to Example 1, wherein the channel is configured to enable flow at any angle relative to horizontal.

Example 18 relates to the microfluidic device according to Example 1, wherein the channel is defined along a surface of a needle.

Example 19 relates to the microfluidic device according to Example 18, wherein the first channel is coupleable to a second microscale channel on a surface of a base that is coupleable to the needle.

Example 20 relates to the microfluidic device according to Example 1, wherein a ratio of the cross-sectional length of the free interface to the cross-sectional length of the wetted surface decreases along a length of the first channel, whereby a droplet of fluid added to an inlet of the channel is self-propelled along the length of the first channel.

Example 21 relates to the microfluidic device according to Example 1, further comprising a second cross-section and a transition between the first and second cross-sections. The second cross-section is greater in size in comparison to the first cross-section. The transition causes pinning of the flow of fluids, such that the flow is only enabled when liquid is provided downstream of the geometry change.

Example 22 relates to the microfluidic device according to Example 1, wherein the first channel is in fluid communication with a common area, wherein at least one additional channel is also in fluid communication with the a common area, thereby allowing device filling independent of synchronized fluid additions.

Example 23 relates to the microfluidic device according to Example 1, wherein the first channel comprises material positioned on a surface of the first channel, whereby the material is configured to incorporate into solution when a fluid flows through the first channel.

In Example 24, a method for using a microscale channel comprises providing fluid to or removing fluid from a first microscale channel. The first channel comprises a first cross-section that comprises a wetted surface comprising hydrophilic material and a free interface comprising an open air-liquid interface. The wetted surface contacts fluid flowing through the channel. The ratio of a cross-sectional length of the free interface and a cross-sectional length of the wetted surface is less than the cosine of the contact angle, thereby permitting spontaneous capillary flow.

Example 25 relates to the method according to Example 24, wherein the providing fluid to the first microscale channel comprises inserting the fluid in the first channel with an automated fluid dispensing system.

Example 26 relates to the method according to Example 25, wherein the automated fluid dispensing system is a manual or automated pipette.

Example 27 relates to the method according to Example 24, wherein the providing fluid to the first microscale channel comprises contacting the first channel with a fluid pooling on a surface, thereby drawing the fluid into the first channel.

Example 28 relates to the method according to Example 27, wherein the fluid is blood and the surface is the surface of the skin.

Example 29 relates to the method according to Example 24, wherein the removing the fluid from the first microscale channel comprises placing the first channel in fluid communication with a second channel, wherein the second channel has a second cross-section with a ratio of a cross-sectional length of a free interface to a cross-sectional length of a wetted surface that is smaller than the ratio of the first cross-section.

Example 30 relates to the method according to Example 24, wherein the providing fluid to the first microscale channel comprises placing an end of the first channel into a second channel, wherein the second channel has a second cross-section with a ratio of a cross-sectional length of a free interface to a cross-sectional length of a wetted surface that is greater than the ratio of the first cross-section.

Example 31 relates to the method according to Example 24, wherein the removing the fluid from the first microscale channel comprises removing a substance from the fluid through an open air-liquid interface window defined in the channel.

Example 32 relates to the method according to Example 31, wherein the removing the substance from the fluid comprises removing magnetic beads by applying a magnetic force at the window.

Example 33 relates to the method according to Example 32, wherein the removing the magnetic beads comprises trapping the beads on a solid surface by placing the solid surface in substantially proximity with or in contact with the surface of the liquid at the window.

Example 34 relates to the method according to Example 31, wherein the removing the substance from the fluid comprises extracting particles from the fluid by contacting the fluid with an immiscible fluid at the window.

Example 35 relates to the method according to Example 31, wherein removing the substance from the fluid comprises removing particles by trapping the particles on a material placed in contact with the fluid interface at the window, wherein the material comprises compounds configured to bind the particles.

In Example 36, a method for using a microscale channel comprises moving fluid within a first microscale channel. The first channel comprises a first cross-section that comprises a wetted surface comprising hydrophilic material and a free interface comprising an open air-liquid interface. The wetted surface contacts fluid flowing through the channel. The ratio of a cross-sectional length of the free interface and a cross-sectional length of the wetted surface is less than the cosine of the contact angle, thereby permitting spontaneous capillary flow.

Example 37 relates to the method according to Example 36, wherein the moving fluid within the first channel comprises urging fluid through the first channel and at least one other channel into a common channel or holding chamber, wherein flow within each of the first channel and the at least one other channel are independent, thereby allowing a combination of different flows without air bubble formation.

Example 38 relates to the method according to Example 36, wherein the first channel comprises a flow control location comprising a flow control cross-section comprising a ratio of free interface to wetted surface that is greater than the cosine of the contact angle, the method further comprising reducing the ratio of the flow control cross-section to a value smaller than the cosine of the contact angle.

Example 39 relates to the method according to Example 38, wherein the reducing the ratio of the flow control cross-section further comprises adding an immiscible fluid to the channel such that the immiscible fluid spans a portion of the free interface of the first channel.

Example 40 relates to the method according to Example 38, wherein the reducing the ratio of the flow control cross-section further comprises displacing a material that covers a portion of the free interface of the first channel.

Example 41 relates to the method according to Example 38, wherein the reducing the ratio of the flow control cross-section further comprises displacing at least one wall of the first channel, thereby reducing a length of the free interface.

Example 42 relates to the method according to Example 36, wherein the moving the fluid within the first channel further comprises causing the fluid to flow on a first plane oriented at any angle, and causing the fluid to traverse to a second plane with a connector oriented at any angle relative to the first plane.

Example 43 relates to the method according to Example 42, wherein the connector comprises an open microfluidic channel having only two wetted surfaces.

Example 44 relates to the method according to Example 36, wherein the moving the fluid within the first channel further comprises causing the fluid to flow over a heterogeneous area disposed on a wall of the first channel.

Example 45 relates to the method according to Example 44, wherein the area is an open liquid-air interface.

Example 46 relates to the method according to Example 44, wherein the area is an absorbent material, thereby causing the absorption of a defined fluid volume.

Example 47 relates to the method according to Example 44, wherein the area is a second immiscible fluid.

Example 48 relates to the method according to Example 36, wherein the moving the fluid within the first channel further comprises causing the fluid to flow over an opening in a bottom portion of the first channel such that the fluid is in fluid communication with ambient air on a top portion and the bottom portion of the first channel.

Example 49 relates to the method according to Example 36, wherein the moving the fluid within the first channel further comprises applying a reagent in dried form on the surface of the first channel such that the reagent dissolves into the fluid as the fluid is moved through the channel.

Example 50 relates to the method according to Example 36, wherein the moving the fluid within the first channel further comprises coating at least a portion of at least one wall of the first channel with a reagent, wherein the reagent comprises particles of interest.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 10A is a perspective view of a Y channel allowing two sources of fluid to join and in which one branch can be filled before the other branch without the risk of creating an air bubble, according to an exemplary embodiment.

FIG. 10B is a perspective view of a Y channel allowing two sources of fluid to join and in which one branch can be filled before the other branch without the risk of creating an air bubble, according to an exemplary embodiment.

FIG. 10C is a perspective view of a Y channel allowing two sources of fluid to join and in which one branch can be filled before the other branch without the risk of creating an air bubble, according to an exemplary embodiment.

FIG. 10D is a perspective view of a Y channel allowing two sources of fluid to join and in which one branch can be filled before the other branch without the risk of creating an air bubble, according to an exemplary embodiment.

FIG. 14A is a perspective view of an exemplary embodiment of the system enabling the application of a substance to an open microfluidic channel or reservoir to apply treatments to a contained fluid.

FIG. 14B is a perspective view of the embodiment of FIG. 14A, showing the substance applied to the fluid.

FIG. 14C is a perspective view an alternative exemplary embodiment of the system enabling the application of a substance to an open microfluidic channel or reservoir to apply treatments to a contained fluid.

FIG. 14D is a perspective view of the embodiment of FIG. 14C, showing the substance applied to the fluid.

DETAILED DESCRIPTION

Figure 1A:
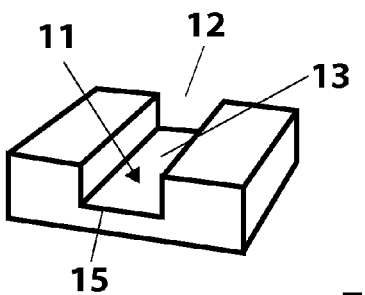
FIG. 1A is a perspective view of an exemplary embodiment of a microchannel containing an open interface.

The various systems and devices disclosed herein relate to devices for use in medical procedures and systems. More specifically, various embodiments relate to various medical devices, including open devices, methods and systems relating to a microfluidic network.

It is understood that the various embodiments of the devices and related methods and systems disclosed herein can be incorporated into or used with any other known medical devices, systems, and methods. For example, the various embodiments disclosed herein may be incorporated into or used with any of the medical devices and systems disclosed in co-pending U.S. application Ser. No. 13/750,526, filed Jan. 25, 2013, entitled "Handheld Device for Drawing, Collecting, and Analyzing Bodily Fluid," which claims priority to U.S. Application No. 61/590,644, filed Jan. 25, 2012, entitled "Handheld Device for Drawing, Collecting, and Analyzing Bodily Fluid," all of which are hereby incorporated herein by reference in their entireties.

Referring generally to the figures, an "open microfluidic groove" is defined as a channel with a cross-section containing one or more sections for which the fluid spans over an open air-liquid interface and one or more sections for which the fluid contacts a hydrophilic material. The open microfluidic groove will also be referred to herein as an open microfluidic groove, an open microfluidic network, an open microfluidic channel, a microfluidic channel, a microfluidic groove, or more generally as a channel or a groove. It is understood that one or more grooves or channels can make up a network. At each point in the microfluidic groove, the length of the section of the cross-section contacting hydrophilic material is called the wetted perimeter, and the length of the remaining section is called the free perimeter. Further, the SCF relation, determining whether spontaneous capillary flow occurs in the open microfluidic channel, states that the ratio of the free perimeter and the wetted perimeter of the microfluidic groove must be less than the cosine of the contact angle of the fluid on the hydrophilic material constituting the walls of the microfluidic groove. A microfluidic groove designed for performing a specific function or assembled with other microfluidic components is called an open microfluidic network.

Leveraging the open aspect of the microfluidic groove as well as surface tension phenomena, a variety of fluidic components can be developed allowing the control of the flow through the microfluidic groove and the creation of larger open microfluidic networks. The design rule stating that the ratio of the free perimeter and the wetted perimeter of the microfluidic groove is less than the cosine of the contact angle of the fluid, allows the design of microfluidic channels containing several open liquid-air interfaces, or channels that do not require the totality of the wetted perimeter to operate (and thus can still flow if partly blocked by an air bubble or a ridge in the fabrication). Open microfluidic channel or microfluidic grooves can be designed as a channel with a U-shaped cross-section devoid of a ceiling, or a channel with a rectangular cross-section devoid of a ceiling and floor for example. Another example is a channel with a rectangular cross-section devoid of a ceiling and containing circular apertures in its floor. Certain other embodiments include channels with a V-shaped cross-section, trapezoidal cross-sections, rounded or multi-indented cross-sections. These channel embodiments enable the design of channels that allow straightforward access for inserting or removing substances from the microfluidic network.

Typical microfluidic approaches contain several inherent challenges that limit their reliability and ease-of-use for diagnostic, handheld, and analysis applications. One of these challenges is the difficulty of fabricating fully enclosed microfluidic channels, often requiring a bonding step. Open microfluidic channels resolve this issue, as they allow the creation of microfluidic networks that can be fabricated in one simple embossing step. A second challenge of typical microfluidic networks is the formation and entrapment of air bubbles, often synonymous of a critical failure of the whole microfluidic system. A common workaround involves the placement of air escapes to allow trapped air bubbles to escape, thus maintaining the fluidic connection within the microfluidic channel. Open microfluidic networks solve these prior art limitations by allowing at all locations air bubbles to escape.

A third challenge in microfluidic systems is the interconnection between the microscale channel and the macroscale real world. In most traditional microfluidic systems, the fabrication of a usable device relies on establishing a water- or air-tight connection between a tube leading into the microfluidic device and the device itself. Open microfluidic channels allow the input and output of fluid into and from a channel by simply putting a drop of fluid in contact with the channel or inserting a second open microfluidic network in a first one. Further, open microfluidic channels enable the removal of particles from the fluid contained in the open microfluidic channel by leveraging the open interfaces for extraction by means of magnetic, diffusion, physical, or other interaction forces.

Referring now to the figures, the devices, systems and methods pertaining to the use of an open microfluidic network will be described in detail. FIG. 1A-FIG. 1D are perspective views of various exemplary embodiments of open microfluidic channels 11. These open microfluidic channels 11 typically involve at least one free surface 12 and at least one wetted surface 13 defining boundaries of a cross section 15 known as the "free perimeter" (at 12) and "wetted perimeter," (at 13) respectively. In certain exemplary embodiments, the cross-section 15 of the microfluidic channel 11 verifies the SCF relation stating that the ratio of the length of the cross-section spanning over the at-least one free surface 12 to the length of the cross-section spanning over the at-least one wetted surface 13 is less than the cosine of the contact angle 14A of the fluid 14 on the wetted surface 13, ensuring that fluid 14 spontaneously flows by capillary force along channel 11.

Figure 1B:
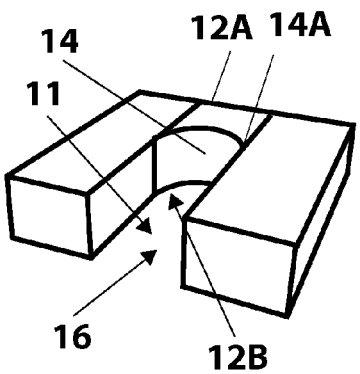
FIG. 1B is a perspective view of an exemplary embodiment of a microchannel containing an open interface.
Figure 1C:
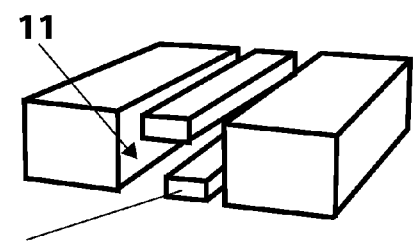
FIG. 1C is a perspective view of an exemplary embodiment of a microchannel containing an open interface.
Figure 1D:
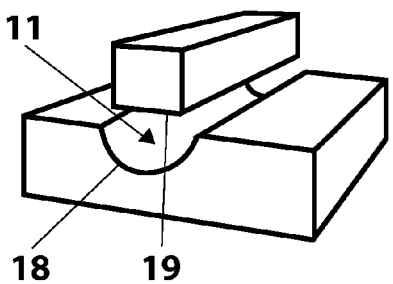
FIG. 1D is a perspective view of an exemplary embodiment of a microchannel containing an open interface.
Figure 1E:
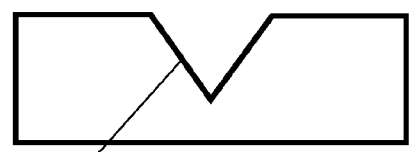
FIG. 1E is a sidelong view of an exemplary embodiment of a microchannel containing an open interface.
Figure 1F:
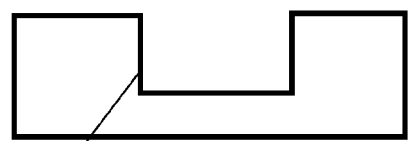
FIG. 1F is a sidelong view of an exemplary embodiment of a microchannel containing an open interface.
Figure 1G:
FIG. 1G is a sidelong view of an exemplary embodiment of a microchannel containing an open interface.

The depicted embodiments are of a fluidic channel with one open interface in a channel with a rectangular cross-section 15 (as shown in FIG. 1A), of a fluidic channel in a parallel rail embodiment 16 having a first 12A and second 12B free surface, or interface (as shown in FIG. 1B), of a fluidic channel with various free and wetted surfaces 17 (as shown in FIG. 1C), of a fluidic channel with a curved surface 18 and a second contacting surface 19 (as shown in FIG. 1D), all of which allow fluid to freely flow within the channel 11. However, other embodiments involving free surfaces 12 and wetted surfaces 13 can be enabled using this technique and can involve wedge channels, channels with apertures, channels with a V-shaped cross-section 20 (as shown in FIG. 1E), channels with a U-shaped cross-section 21 (as shown in FIG. 1F), and channels with a rounded U-shaped cross section 21a (as shown in FIG. 1G), among others. Furthermore, the V-shaped cross-section depicted in FIG. 1E allows the creation of open microfluidic grooves that allow the capillary flow of fluids even with part of the wetted perimeter (shown at 13) impaired by factors such as an air bubble, a fabrication defect, or a local hydrophilic treatment defect.

Figure 1H:
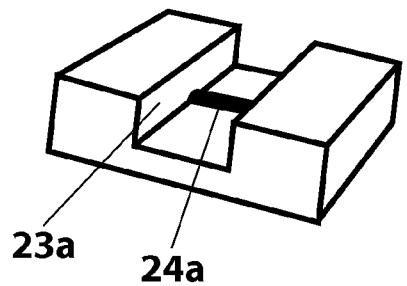
FIG. 1H is a perspective view of an exemplary embodiment of a microchannel containing an open interface.

In the exemplary embodiment depicted in FIG. 1H., the walls 23a of an open microfluidic channel 11 validate the design criteria alone such that they enable the flow over a ridge or fabrication defect 24a, that would otherwise have caused the pinning of the fluid at that location and thus the blockage of the channel. Other embodiments are possible.

Figure 2A:
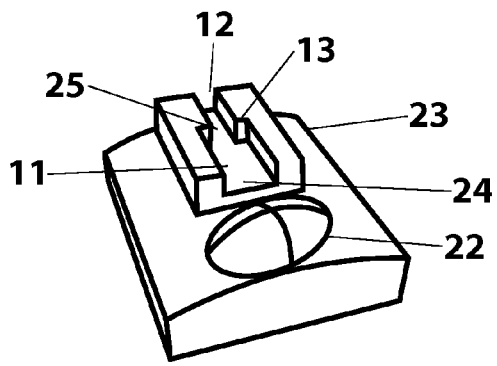
FIG. 2A is a perspective view of an exemplary embodiment of a microfluidic channel used to collect fluid pooling on a surface.

FIGS. 2A-2D are perspective views of an open microfluidic channel 11 that comes into contact with a pooling fluid 22 that exists on a surface 23. The pooling fluid 22 can be blood, and the liquid can be pooling on a surface 23 such as the skin. By way of example, and as depicted in FIG. 2A, the open microfluidic channel 11 may contain a capture region 24 and a channel region 25 that are connected and can allow the fluid 22 to flow into the channel. The open microfluidic channel 11 is composed of free surfaces 12 and wetted surfaces 13 satisfying the SCF relation, stating that the ratio of the length of the cross-section of channel 11 spanning over the at-least one free surface 12 to the length of the cross-section of channel 11 spanning over the at-least one wetted surface 13 is less than the cosine of the contact angle of the fluid 14 on the wetted surface 13.

Figure 2B:
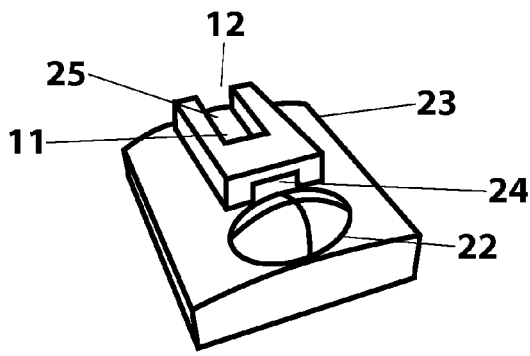
FIG. 2B is a perspective view of an exemplary embodiment of a microfluidic channel used to collect fluid pooling on a surface.
Figure 2C:
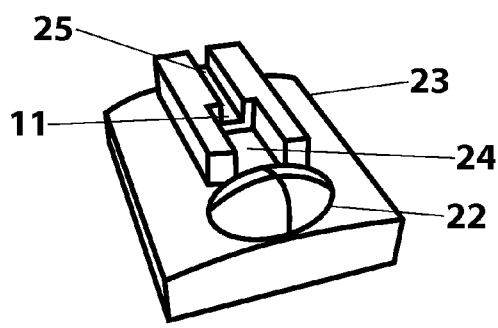
FIG. 2C is a perspective view of an exemplary embodiment of a microfluidic channel used to collect fluid pooling on a surface.
Figure 2D:
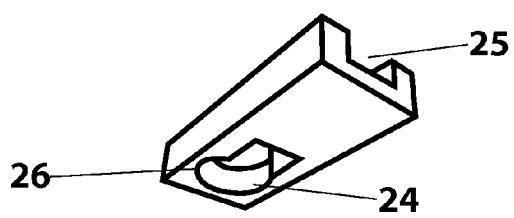
FIG. 2D is an underside perspective view of a microfluidic channel used to collect fluid pooling on a surface according to an exemplary embodiment.

The device embodiments described in FIGS. 2A-2C can be used, for example, by placing the capture region 24 of the open microfluidic channel 11 in contact with the pooling fluid 22 on a surface 23, allowing fluid to freely pull into the microfluidic channel 11. Upon completely removing the fluid, or when the user desires, the channel 11 is disconnected from fluid 22 and the flow of fluid in the channel ceases. In the embodiment described in FIG. 2D, an expanded open area 26 is designed at the capture region 24 to facilitate the contact of the open microfluidic network with the blood pooling on the surface.

In FIG. 2A, the capture region 24 and the channel region 25 are represented by an open channel devoid of a ceiling or top portion, the extremity of which can contact a fluid 22. The capture region 24 is wider than the channel region 25 in order to facilitate broad capture of a pooling fluid. In alternative embodiments the walls of the capture region 24 can be raised or extended to allow the creation of a wider caption region 24.

In the alternate embodiment described in FIG. 2B, the capture region 24 is open near the surface 23 (or "bottom") in order to facilitate the capture of a pooling fluid 22. The channel region 25 is open away from the surface 23 (or "top") in order to prevent the exposure of fluid to the surface 23. The transition from the capture region 24 and the channel region 25 may be comprised of a small section of channel open both to the top and the bottom, by an immediate transition from open to the top to open to the bottom, or by an overlapping region in which the channel 11 is both closed on top and on bottom.

In the alternate embodiment described in FIG. 2C, the capture region 24 is open to both the top and the bottom relative to the surface 23, thus allowing the capture of fluid 22, and connection to the channel region 25 open only at the top, in order to prevent exposure of the fluid to the surface 23. These embodiments may be developed with cross-sectional geometries of the channel 11, the channel region 25, or the capture region 24, so as to provide a higher wetted surface 13. By way of example, such embodiments may include V-shaped, trapezoidal-shaped, or crenated-shaped cross-sections.

Figure 3A:
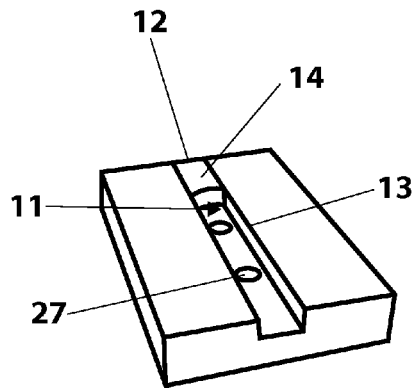
FIG. 3A is a perspective view of an open microfluidic channel with an open interface used to extract particles in fluid or a portion of the fluid itself from the channel according to one exemplary embodiment.

FIGS. 3A-3D are various perspective views of certain embodiments of the open microfluidic channel 11 for use for removing fluid or components of those substances from within an open microfluidic platform. FIG. 3A illustrates an open microfluidic channel 11 with apertures 27 open to another environment, such as a solvent, an oil, a gas, a hydrogel, or another substance. The open microfluidic channel 11 follows the SCF relation such that the ratio of the length of the cross-section of the channel 11—spanning over the at least one free surface 12, including the opening of the aperture 27—to the length of the cross-section of channel 11—spanning over the at-least one wetted surface 13—is less than the cosine of the contact angle of the fluid 14 on the wetted surface 13. These embodiments allow any analytes present in the fluid 14 flowing in the microfluidic groove to flow over the aperture 27, so that they may be extracted from, or viewed in the fluid 14 through the apertures 27.

Figure 3C:
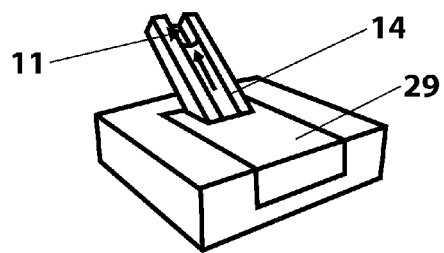
FIG. 3C is a perspective view of an open microfluidic channel with an open interface used to extract particles in fluid or a portion of the fluid itself from the channel according to one exemplary embodiment.
Figure 3B:
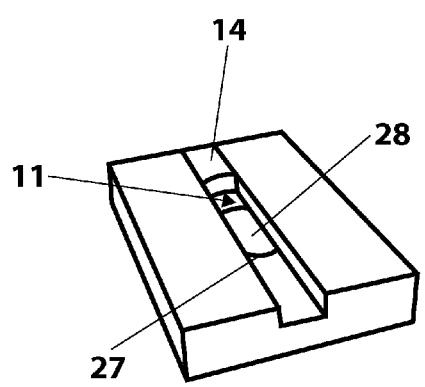
FIG. 3B is a perspective view of an open microfluidic channel with an open interface used to extract particles in fluid or a portion of the fluid itself from the channel according to one exemplary embodiment.

FIG. 3B. is a perspective view of an embodiment of the open microfluidic channel 11 further comprising a pad 28 in the center of the channel 11 such that analyte fluid 22 or fluid 14 is extracted through the bottom of the channel as fluid 14 passes over the pad 28. It is understood that capillary flow occurs over the channel 11 (even in the absence of the pad 28), thereby ensuring a reliable connection between the fluid 14 in the channel 11 and the pad 28.

FIG. 3C depicts a suspended channel 11 dipping into an open reservoir 29 such that a fluid 14 is extracted from the reservoir 29 into the open microfluidic network (as designated by the channel 11).

Figure 3D:
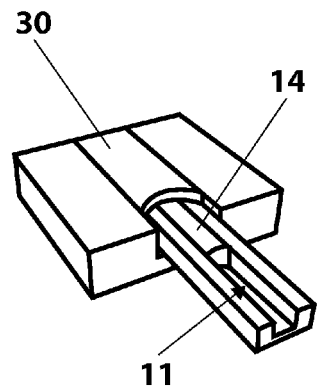
FIG. 3D is a perspective view of an open microfluidic channel with an open interface used to extract particles in fluid or a portion of the fluid itself from the channel according to one exemplary embodiment.

FIG. 3D shows an alternate exemplary embodiment wherein a first open channel 11 is placed within a second open channel 30, thus allowing fluid flowing down the first channel 11 to contact the second channel 30 and flow along that second channel 30. Other embodiments facilitating the exchange of fluid between a first open microfluidic network and a second microfluidic network can be devised. One concept is to have the wetted surfaces of the second microfluidic network extend over the free surfaces of the first microfluidic network, such that the fluid can be driven by spontaneous capillary flow in contact with the surfaces of the second network and subsequently the fluid can be flowed along the second fluidic network. The latter embodiment can be achieved using interdigitated open microfluidic networks for instance.

Figure 4A:
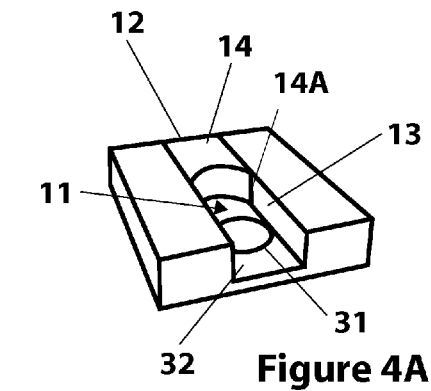
FIG. 4A is a perspective view of liquid in an open microfluidic channel, the liquid flowing over a heterogeneous patch in the wall of the channel, according to certain exemplary embodiments.

FIG. 4A is a perspective view of an exemplary embodiment showing a fluid 14 having a contact angle 14A entering the open microfluidic channel 11 and flowing over a heterogeneous area 31 in the wetted surface 13 of the microfluidic channel 11, which in various embodiments can be an open interface, an absorbent pad, or an immiscible fluid. In these embodiments, the open microfluidic channel 11 is designed to allow a wetted surface 13 that can operate without a floor 32, thus allowing fluid 14 to flow over the heterogeneous patch 31. An analyte 33 can be extracted from the fluid 14 through contact with the heterogeneous patch by means of a capture mechanism which could be a hydrogel laden with a capture substance, a pad containing a capture substance, a magnet, or another solid-phase capture system. The heterogeneous patch could also be a transparent material allowing optical access to the analyte 33 dissolved in the fluid 14.

Figure 4B:
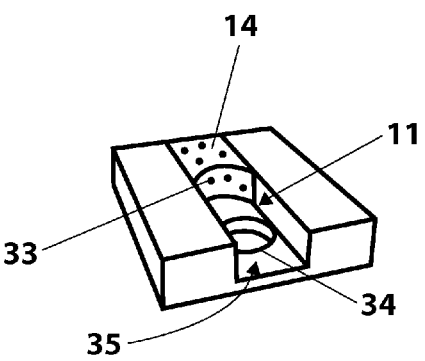
FIG. 4B is a perspective view of liquid in an open microfluidic channel, the liquid flowing over a heterogeneous patch in the wall of the channel, according to certain exemplary embodiments.

FIG. 4B is a perspective view of an embodiment of the heterogeneous patch described in relation to FIG. 4A. In these exemplary embodiments, an aperture 34 connects the fluid 14 flowing in the channel 11 to another fluidic or gaseous environment 35. This second fluidic environment 35 can be a specific liquid or gaseous phase to extract a chemical component contained in the fluid 14 or a fraction of the fluid 14, as desired.

Figure 4C:
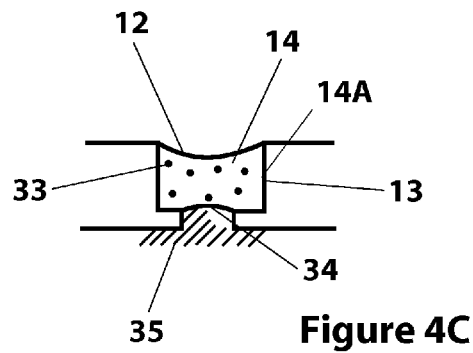
FIG. 4C is a cross-sectional view of liquid in an open microfluidic channel, the liquid flowing over a heterogeneous patch in the wall of the channel, according to certain exemplary embodiments.

FIG. 4C is a cross-sectional view of the embodiment in FIG. 4B. Illustrating the open microfluidic channel 11 with wetted surface 13 and two free surfaces 12, including the aperture 34. The fluid 14 is able to flow over the aperture 34 as the channel validated the SCF relation stating that the ratio of the length of the cross-section of channel 11 spanning over the at-least one free surface 12, including the opening of the aperture 34, to the length of the cross-section of channel 11 spanning over the at-least one wetted surface 13 is less than the cosine of the contact angle 14A of the fluid 14 on the wetted surface 13.

Figure 4D:
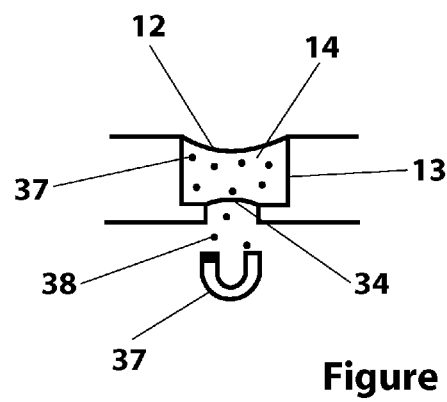
FIG. 4D is a cross-sectional view of liquid in an open microfluidic channel, the liquid flowing over a heterogeneous patch in the wall of the channel, according to certain exemplary embodiments.

In the alternate embodiment depicted in FIG. 4D, magnetic beads 37 in the fluid 14—used to bind an analyte of interest—are carried by the fluid 14 and extracted 38 into the environment outside of the channel by means of a magnetic force, as created by the magnetic beads 37 for instance. Once extracted from the microfluidic groove, the beads out of the fluid 14 can be placed into a diagnostic device or equipment for chemical or molecular analysis. Other means of bead extraction are well-known by those of skill in the art and can be incorporated into the device.

Figure 4E:
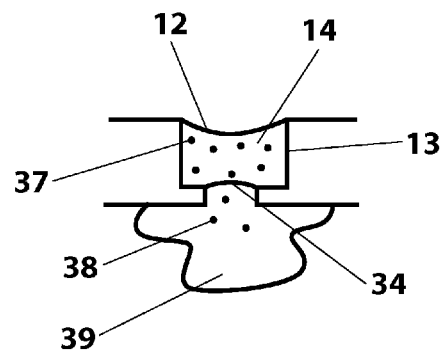
FIG. 4E is a cross-sectional view of liquid in an open microfluidic channel, the liquid flowing over a heterogeneous patch in the wall of the channel, according to certain exemplary embodiments.

In the embodiment depicted in FIG. 4E, a fluid 14 flows over an immiscible fluid 39, at the location of the aperture 34. The contact of the two fluids allows the extraction of beads 38 through diffusion or other electrical forces, of an analyte 37 carried by the fluid 14. Once in the immiscible phase, the analyte 33 can be removed from the microfluidic network for subsequent analysis or flowed to an analysis region or component.

Figure 5A:
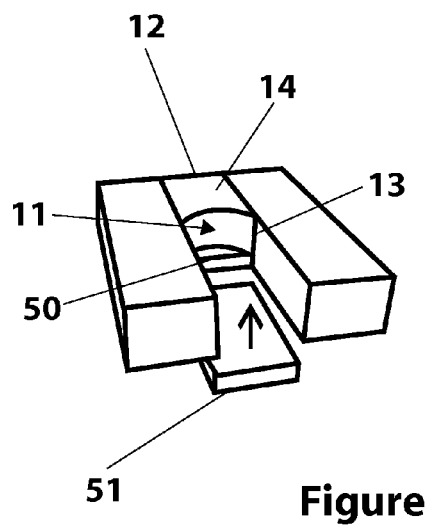
FIG. 5A is a perspective view of an open microfluidic channel in which a material is either placed in contact with the open interface section of the microfluidic channel or distant of it, allowing the controllable flow through the microchannel, according to one embodiment.
Figure 5C:
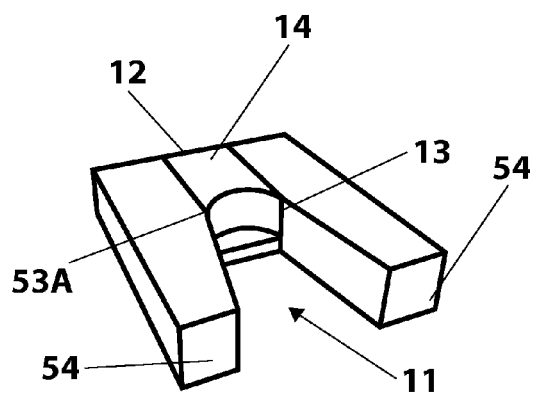
FIG. 5C is a perspective view of an open microfluidic channel in which a force applied to the channel can reduce or increase the free perimeter at a certain location, thereby enabling or preventing the flow of a fluid in the channel, respectively, according to one embodiment.
Figure 5B:
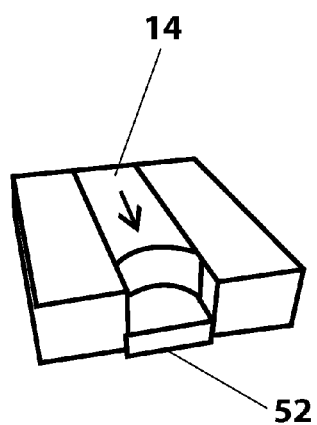
FIG. 5B is a perspective view of an open microfluidic channel in which a material is either placed in contact with the open interface section of the microfluidic channel or distant of it, allowing the controllable flow through the microchannel, according to one embodiment.

FIGS. 5A-5B are perspective views of an exemplary embodiment comprising an open microfluidic channel 11 controllably allowing fluid flow along its length depending on the position of a material closing part of a free interface in the cross-section of channel 11. An open microfluidic channel, or network (shown at the channel 11), with a U-shape cross-section with hydrophilic walls (wetted surfaces 13) and an open liquid-air interface (or free surface 12) on the ceiling validates the design criteria stating that the ratio of the length of the cross-section of channel 11 spanning over the at-least one free surface 12, including the opening of the aperture 27, to the length of the cross-section of channel 11 spanning over the at-least one wetted surface 13 is less than the cosine of the contact angle of the fluid 14 on the wetted surface 13, allows a fluid to flow along its length. At a certain point in the length of the microfluidic channel the cross-section is changed such that it does not validate the SCF relation anymore. The change can be gradual or abrupt, such that the fluid stops advancing at a specific location along the channel 11. In the case of an abrupt change, a ridge 50 causes the pinning of the advancing fluid 14 at a defined location. A displaceable material is allowed to move from a position 51 non-contiguous to the open microfluidic groove, displayed in FIG. 5A, to a position 52 contiguous to the microfluidic groove, displayed in FIG. 5B. When the material is moved from the open position 51 to the closed position 52, through the instruction of a user or an electronic circuit, it is allowed to be in contact with the fluid 14 flowing in the microfluidic groove, thus adding to the wetted perimeter (shown at 13) of the microfluidic groove and causing a variation of the ratio of the free perimeter (shown at 12) to the wetted perimeter. The system can be designed such that this ratio varies from a first value less than the cosine of the contact angle of the fluid to a second value higher than the cosine of the contact angle of the fluid, thus enabling spontaneous capillary flow. Finally, the fluid 14, flowing in the open microfluidic groove, originally blocked in the channel when the material is positioned in the open position 51, can flow over the material when it is positioned in the closed position 52, and continue along the open microfluidic channel 11. The material used to perform the switching from a geometry not validating the SCF relation condition to a geometry validating the SCF relation and thus allowing spontaneous capillary flow can be either a solid plastic, a hydrogel, or another miscible or immiscible fluid.

Figure 5D:
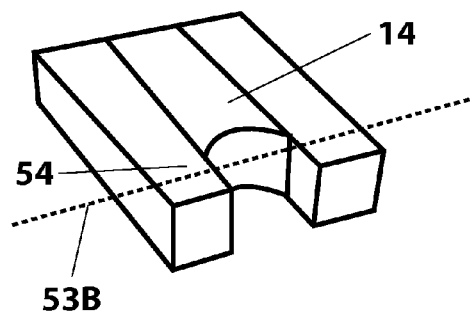
FIG. 5D is a perspective view of an open microfluidic channel in which a force applied to the channel can reduce or increase the free perimeter at a certain location, thereby enabling or preventing the flow of a fluid in the channel, respectively, according to one embodiment.

An alternative embodiment is shown in FIGS. 5C and 5D, in which the fluid 14 is stopped at a specific location (shown at 53A) in the microfluidic channel wherein the geometry of the open microfluidic channel does not validate the SCF relation, which states that the ratio of the length of the cross-section of the channel 11—spanning over the at-least one free surface 12, including the opening of the aperture 27—to the length of the cross-section of the channel 11—spanning over the at-least one wetted surface 13—is less than the cosine of the contact angle of the fluid 14 on the wetted surface 13. When a user actuated force is imparted on the open microfluidic channel, displayed in FIG. 5C, causing the displacement of the walls 54 of the microfluidic channel 11, displayed in FIG. 5D, the aforementioned ratio is decreased to a value less than the cosine of the contact angle of the fluid in the microfluidic channel, and the flow is allowed to continue along the length of the channel 11 (as shown at 53B).

Figure 6A:
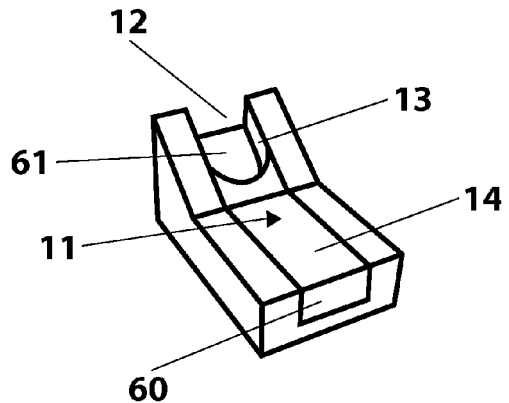
FIG. 6A is a perspective view of a liquid flowing in an open microfluidic channel starting at one plane and bringing the fluid in an open microfluidic channel on a second plane, according to certain exemplary embodiments.

FIG. 6A is a perspective view of a fluid 14 flowing in an open microfluidic channel 11 starting at a first plane 60 and flowing around an angle or curved plane into a continuation of the microfluidic groove on a new plane 61 different from the first plane 60. Importantly in these embodiments the angle of the two planes is less than 180 degrees. In this embodiment, the open microfluidic channel needs to satisfy the SCF relation, which states that the ratio of the length of the cross-section of the channel 11 spanning over the at-least one free surface 12, including the opening of the aperture 27, to the length of the cross-section of the channel 11 spanning over the at-least one wetted surface 13 is less than the cosine of the contact angle of the fluid 14 on the wetted surface 13.

Figure 6B:
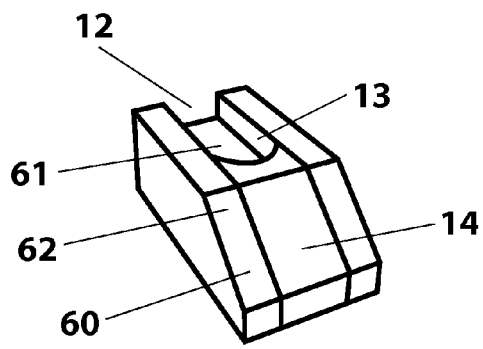
FIG. 6B is a perspective view of a liquid flowing in an open microfluidic channel starting at one plane and bringing the fluid in an open microfluidic channel on a second plane, according to certain exemplary embodiments.

In the embodiment shown in FIG. 6B, the angle between the first plane 60 and the second plane 61 is more than 180 degrees. Specifically, this embodiment prevents the pinning of fluid at the curvature line 62 by ensuring that the microfluidic channel 11 meets a more stringent SCF relation equivalent to that used for an open microfluidic channel devoid of both a ceiling and a wall or floor. Essentially, these embodiments allow the fluid 14 to flow past the curvature line 62 by the capillary force provided by the walls of the channel alone.

Figure 6C:
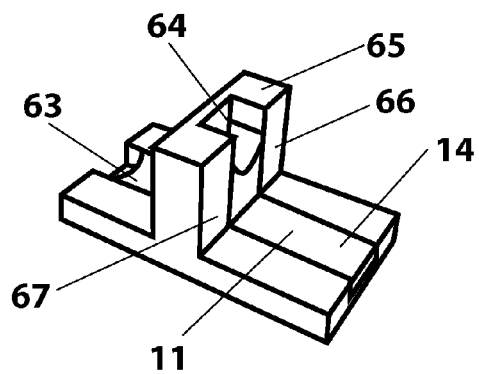
FIG. 6C is a cross-sectional view of a liquid flowing in an open microfluidic channel starting at one plane and bringing the fluid in an open microfluidic channel on a second plane, according to certain exemplary embodiments.

In the embodiment depicted in FIG. 6C, a microfluidic channel 11 open on top is defined on a planar surface 63, and is designed according to the aforementioned SCF relation, thus ensuring the flow of fluid in the microfluidic channel. At a certain location in the first channel 11, a second microfluidic channel 64 build in a plane 65 intersects the channel 11. The SCF relation allows the creation of a junction between the first channel 11 and second channel 64 such that fluid can flow both through the first channel 11 and along the second channel 64. In order to achieve this, the second channel 64 extends into the first channel 11 using, at least in part, a channel that is devoid of both ceiling and floor, such that the fluid can flow by capillary flow using the two side walls 66, 67. This system allows splitting the fluid flowing in the microfluidic network between a microfluidic network with a certain function and a second microfluidic network stacked on top of the first one and connected to it through a vertical open connector system.

Figure 7A:
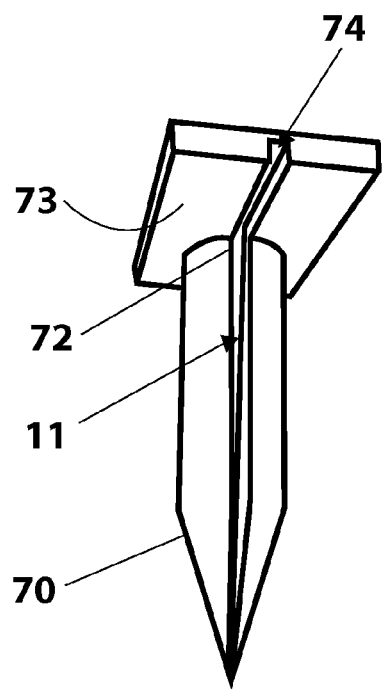
FIG. 7A is a perspective view of an open microchannel defined in a needle that connects into a second open microfluidic channel at the base of the needle, according to one exemplary embodiment.
Figure 7B:
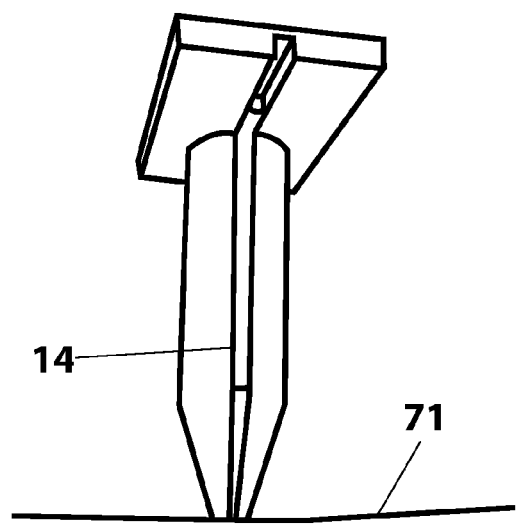
FIG. 7B is a perspective view of an open microchannel defined in a needle that connects into a second open microfluidic channel at the base of the needle, according to the exemplary embodiment of FIG. 7A.

FIGS. 7A-7B are perspective views of various exemplary embodiments comprising an open microfluidic channel 11, which again validates the SCF relation—stating that the ratio of the free perimeter to the wetted perimeter is lower than the cosine of the contact angle, placed along a needle 70 that is designed to penetrate a membrane 71, such as the skin of a user or a membrane covering a reservoir of fluid. When the needle (originally non-contacting the membrane 71 as depicted in FIG. 7A), pierces the membrane 71 and accesses a fluid 14, such as blood or a reagent, the fluid 14 is able to flow into the microfluidic channel 11 along the side of the needle 70, as depicted in FIG. 7B. At the base 72 of the needle 70, the needle contacts a surface 73 containing an open microfluidic groove 74. These embodiments also validate the SCF relation for the given fluid 14. The open microfluidic channel 11 in the needle contact the open microfluidic groove 74 in the base surface in the same plane or at an angled junction such that a fluid 14 can flow along from the microfluidic channel 11 into the microfluidic groove 74. The microfluidic network thus allows drawing fluid from a source protected by a membrane, through a tailored needle, and into an open microfluidic network containing other analysis, chemistry, or diagnostic fluidic components. Furthermore, such a system allows the constant drawing of a fluid 14 into a microfluidic network that may have active or passive analysis components.

Figure 8A:
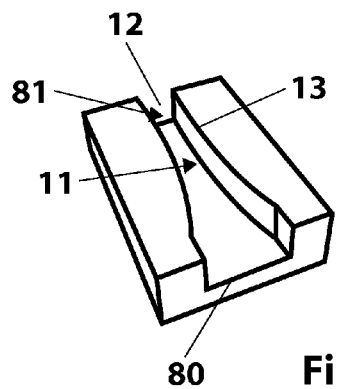
FIG. 8A is a perspective view of an exemplary embodiment of an open microfluidic channel with cross-sections that progressively narrow, according to an exemplary embodiment.
Figure 8B:
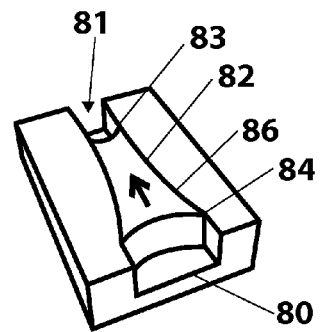
FIG. 8B is a perspective view of an exemplary embodiment of an open microfluidic channel with cross-sections that progressively narrow, according to an exemplary embodiment.

FIGS. 8A-8B are perspective views of an open microfluidic channel 11 with a cross-section of the wetted surface 13 that progressively narrows from a wide configuration end 80 to a narrow configuration end 81, as shown in FIG. 8A. At all points, however, the free surface cross sectional area 12 to the wetted surface cross sectional area 13 is less than the cosine of the contact angle between the fluid to be flowed in the channel and the wetted surface 13. As shown in FIG. 8B, when a droplet of fluid 82 is placed in the microfluidic channel 11, a first side of the droplet (or "leading edge") 83, facing towards the narrow end 81 of the microfluidic channel 11, experiences a ratio of the free cross-section to the wetted cross section less than the second side of the droplet (or "the trailing edge") 84, facing the wider end 80 of the channel 11. In such a system, a droplet of fluid 82, containing at least one open liquid-air interface, will self-propel through the microfluidic channel 11, from the wider end 80 to the narrower end 81. Furthermore, in these embodiments, this can be achieved with one or more open interfaces, such as channels devoid of a ceiling, a ceiling and a floor, or channels devoid of a ceiling and containing apertures in the floor, as would be apparent to one of skill in the art.

Figure 8C:
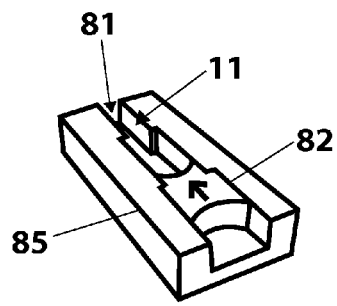
FIG. 8C is a perspective view of an exemplary embodiment of an open microfluidic channel with cross-sections that progressively narrow, according to an exemplary embodiment.
Figure 8D:
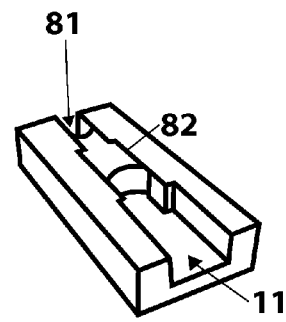
FIG. 8D is a perspective view of an exemplary embodiment of an open microfluidic channel with cross-sections that progressively narrow, according to an exemplary embodiment.

In the embodiment depicted in FIGS. 8C-8D, the change of geometry along the channel length is not gradual, rather it contains finite geometrical steps 85. In these exemplary embodiments, a droplet of fluid 82 inserted in the channel will equally flow along the channel 11, towards the narrower end 81, provided that the geometries of the channel are designed in such a way so as to allow the volume of the fluid to span from a step in the channel to the next step in the channel.

Figure 8E:
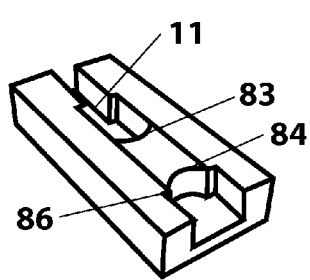
FIG. 8E is a perspective view of an exemplary embodiment of an open microfluidic channel with cross-sections that progressively narrow, according to an exemplary embodiment.
Figure 8F:
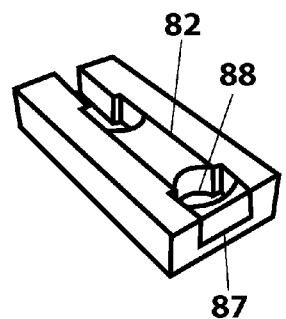
FIG. 8F is a perspective view of an exemplary embodiment of an open microfluidic channel with cross-sections that progressively narrow, according to an exemplary embodiment.
Figure 8G:
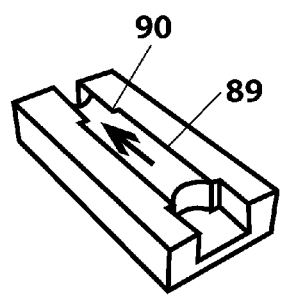
FIG. 8G is a perspective view of an exemplary embodiment of an open microfluidic channel with cross-sections that progressively narrow, according to an exemplary embodiment.

In FIGS. 8E-8G, another embodiment is depicted which allows the creation of open volume controlled valves that only permit fluid flow along a channel provided a sufficient amount of volume is inserted. In FIG. 8E, a droplet of fluid 82 is inserted into the microfluidic channel 11, and through the mechanism described previously, it is able to self-propel forward as long as the ratio of free to wetted perimeter at the leading edge 83 is smaller than the ratio of free to wetted perimeter at the trailing edge 84. When the trailing edge 84 reaches an abrupt change in geometry 86, if the leading edge does not validate the condition described, the droplet of fluid 82 stops.

FIG. 8F. depicts the addition of an additional fluid 87 consisting of an aqueous fluid of similar surface energy, an aqueous fluid of lower surface energy, or an immiscible fluid may be inserted into the channel and will itself flow down the channel 11 in a similar way as the first droplet of fluid 82. The open aspect of the channel will prevent air bubble formation in the channel as air can escape between the two fluids 82 and 87 in the area 88.

As shown in FIG. 8G, if the additional fluid 87 is miscible with the droplet of fluid 82 and contacts the original droplet of fluid 82, the volume of the additional fluid adds to that of droplet and the increased droplet 89 may contain the sufficient volume to contact a subsequent geometrical change 90. If the additional fluid 87 is immiscible with the droplet of fluid 82 and contacts the original droplet of fluid 82, the two droplets connect but do not mix, and the fluid 87 propels the fluid 82 beyond the constriction. With this method of self-microfluidic propulsion, a channel 11 can be devoid of specialized geometries; so long as the immiscible back fluid 87 surface energy is less than the original fluid 82. Once the droplet 89 contacts the geometrical change 90, the whole droplet is able to flow forward into the microfluidic network.

FIGS. 9A-9E are perspective views of embodiments of an first open microfluidic channel 11 with a cross-sectional wetted surface 13 that expands abruptly to a second channel 91 having a wetted perimeter 92, creating a pinning plane 93. Importantly, the two wetted perimeters—the first wetted surface 13 and second channel 91 wetted surface (shown at the flow 97, in FIG. 9E)—must be of different width and height, and both the first channel 11 and second channel 91 geometries must validate the SCF relation that the ratio of the free surface cross sectional area 12 to the wetted surface cross sectional area 13 as less than the cosine of the contact angle between the fluid 14 and the wetted surface 13.

Figure 9A:
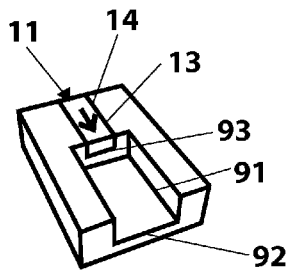
FIG. 9A is a perspective view of an open microfluidic channel with cross-sections that abruptly narrow, thereby enabling the creation of a capillary valve that does not require an air outlet to prevent the formation of air bubbles to operate, according to certain exemplary embodiments.
Figure 9B:
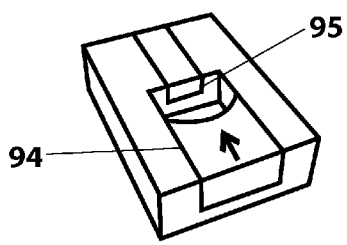
FIG. 9B is a perspective view of an open microfluidic channel with cross-sections that abruptly narrow, thereby enabling the creation of a capillary valve that does not require an air outlet to prevent the formation of air bubbles to operate, according to certain exemplary embodiments.
Figure 9C:
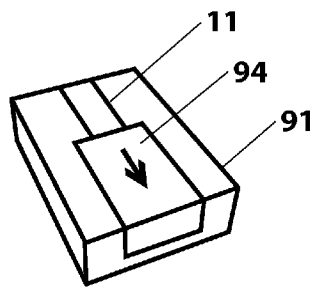
FIG. 9C is a perspective view of an open microfluidic channel with cross-sections that abruptly narrow, thereby enabling the creation of a capillary valve that does not require an air outlet to prevent the formation of air bubbles to operate, according to certain exemplary embodiments.
Figure 9D:
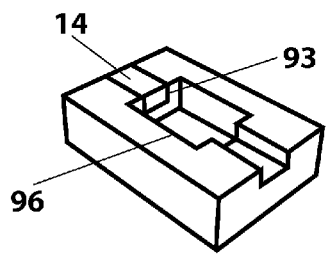
FIG. 9D is a perspective view of an open microfluidic channel with controllable open capillary valve and open area, wherein the open area has not yet filled with fluid because the fluid has pinned, according to certain exemplary embodiments.
Figure 9E:
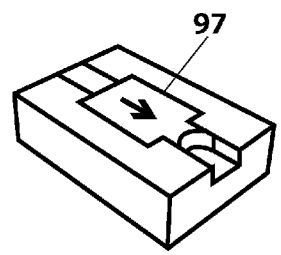
FIG. 9E is a perspective view of the embodiment of FIG. 9D, wherein the addition of fluid has cause flow into the open area.

As shown in FIG. 9A, when a fluid 14 enters the first channel 11, the change in geometry causes fluid pinning on the plane 93. A fluid 94 inserted in the second channel 91 flows in direction of the first channel 11, as the air can escape from the open interfaces 95 of the microfluidic channel, as shown in FIGS. 9B-9C. Upon contact of the fluids 14 and 94, the pinning on plane 93 is released and the fluid can then flow according to the natural pressure gradient generated by capillary force or any other pressure source, as depicted in FIGS. 9D-9E. Reversibly, if the first fluid to enter the network is fluid 94 in the channel 91, no pinning will be observed as the geometry is narrowing instead of increasing.

In the embodiment of FIGS. 9D-9E, a controllable open capillary valve is described. Similarly, a fluid 14 flowing down an open microfluidic channel 11 reaches an abrupt expansion in geometry, causing pinning of the fluid 14 at device plane 93, as depicted in FIG. 9D. An open area 96 allowing the manual or electronically controlled deposition of fluid is placed immediately after the plane 93. When a fluid is added in the area 96, it removes the pinning of fluid 14 on plane 93 and allows the flow 97 to pursue along the channel according to the natural pressure gradient, as shown in FIG. 9E. Conversely, when fluid 14 is removed from area 96, a fluid from the open microfluidic channel 11 can once again pin at the plane 93.

FIGS. 10A and 10B are perspective views of embodiments comprising an open microfluidic network 98 further comprising first and second open microfluidic channels 99, 100 combining into a single combinatorial area, in this case a third channel 101. Each of the first channel 99, second channel 100, and third channel 101 further validate the SCF relation that the ratio of the free surface cross sectional area 12 to the wetted surface cross sectional area 13 as less than the cosine of the contact angle between the fluid 14 and the wetted surface 13 such that spontaneous capillary flow can occur. In these exemplary embodiments, a fluid 102 entering the first channel 99 can flow down the channel, reaches the intersection point between the first channel 99, second channel 100, and third channel 101, and is able to flow down the third channel 101. In certain embodiments, a capillary valve such as is depicted in FIG. 9A can be added to prevent flow down the second channel 100.

In exemplary embodiments, a second fluid 103 can be added to the second channel 100, flow down the channel, without risk of trapping an air bubble as gas can escape through the open interfaces, as depicted in FIG. 10B. Once connected to the fluid 102 in the first channel 99, the second fluid 103 can combine volume to the volume of fluid 102 flowing into the third channel 101 and create a resulting flow 104 comprised of both fluids 102, 103. These embodiments enable the creation of a device combining the fluid from multiple sources that may not deliver fluid synchronously, without the risk of creating air bubbles, so as to combine the liquids delivered by both sources. These embodiments can have applications in mixing fluids in microfluidic networks or for more efficient human bodily fluid collection from multiple sources.

Figure 10E:
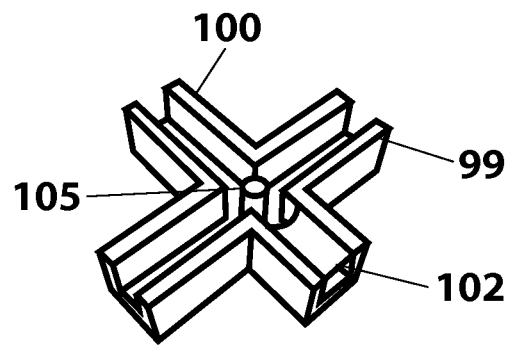
FIG. 10E is a perspective view of a Y channel allowing two sources of fluid to be routed into two other channels, in which one source branch can be filled before the other source branch without the risk of creating an air bubble, according to an exemplary embodiment.
Figure 10F:
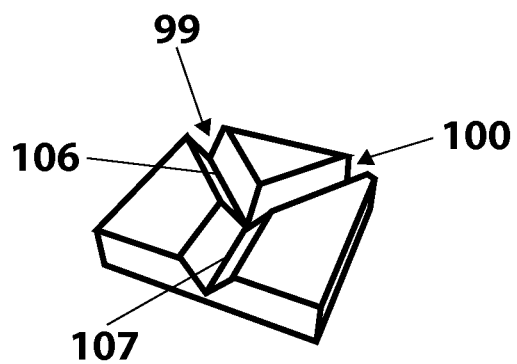
FIG. 10F is a perspective view of a Y channel allowing two sources of fluid to join and in which one branch can be filled before the other branch without the risk of creating an air bubble, according to an exemplary embodiment.
Figure 10G:
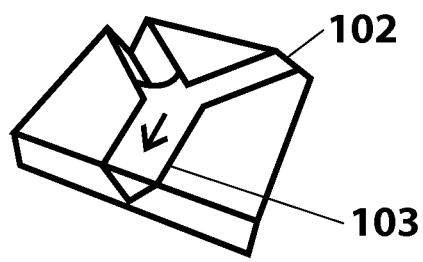
FIG. 10G is a perspective view of a Y channel allowing two sources of fluid to join and in which one branch can be filled before the other branch without the risk of creating an air bubble, according to an exemplary embodiment.

FIGS. 10C-10E describe alternate embodiments in which the connection geometry 105 between the first 99 and second channels 100 is rounded in order to increase the ability of the first fluid 102 to fill the combinatorial area/third channel 101. Similarly FIGS. 10E-10G describe an embodiment using open microfluidic channels that have different profiles, such as the X-shaped cross section of FIG. 10E. By way of example, and as depicted in FIGS. 10F-10G, a V-shaped cross-section 106 allows more reliable connection of the fluids flowing down the first 99 and second channels 100 into the third channel 101. The bottom edge 107 of the V-shaped cross-section enhances the capillary pull along both the connection of the first channel 99 to the third channel 101, and the connection of the second channel 100 to the third channel 101, as the fluid can follow the same single line connecting all these channels together. This method can allow fluid to flow into any third channel area 101, including an open microchannel, a pad, a reservoir, or any other general area for fluid to congregate.

Figure 11A:
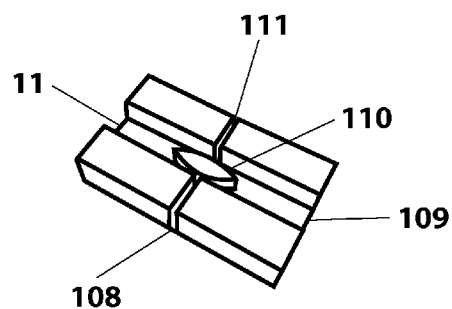
FIG. 11A is a perspective view of a method enabling the flow of fluids from one open microfluidic channel to another, according to one embodiment.
Figure 11D:
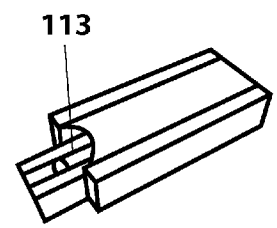
FIG. 11D is a perspective view of the embodiment of FIG. 11C showing fluid flow.
Figure 11B:
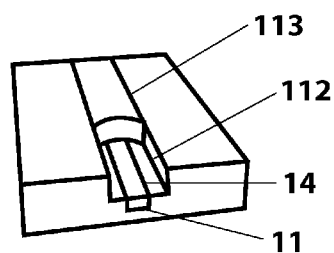
FIG. 11B is a perspective view of an open microfluidic network built inside a larger open microfluidic network, according to one embodiment.

FIG. 11A-11B are perspective views of an alternate embodiment enabling the flow of fluids from one open microfluidic channel to another and reversibly in an approach that allows the building of open microfluidic networks by assembling standardized open microfluidic components. In this method, the open microfluidic channel 11 is ended at an extremity 108 which would stop the flow of fluid due to pinning. In these embodiments, a second open microfluidic channel 109 is placed in close proximity to the first channel 11 and fluid transfer from one channel to the other is enabled through the addition of a structure 110 connected to the second channel 109 and overreaching into channel 11. As fluid is flowing by capillary force along the first channel 11, it is brought in contact with the structure 110, which allows the fluid to bridge over the gap 111 and contact the wetted surfaces of channel 109. Reversibly, the structure 110 will enhance the ability of fluid flowing along channel 109 to contact the walls of the first channel 11.

FIG. 11B is a perspective view of yet another alternate embodiment open microfluidic network inside a larger open microfluidic network. The first channel 11 validated the SCF relation such that fluid 14 is able to flow along its length by capillary force. The first channel 11 is built inside a surface of a second open microfluidic channel 112, which also validates the SCF relation, allowing fluid 113 to flow along the length of channel 112. In these embodiments, a first fluid can be flown into the microfluidic network and be reacted, incubated, or acted upon, and a second carrier fluid or dilution fluid can be flown subsequently. Application of these embodiments may include the dilution a fluid sample of interest such as blood, the insertion of a chemical reagent to react with the fluid sample of interest, or the deposition on the surfaces of a microchannel of a chemical treatment that will react with a fluid sample of interest inserted in the larger channel. In the latter example chemical reagents, such as lysis buffers or anti-clot factors, or sensing/capture materials, such as functionalized hydrogels or magnetic beads, can be deposited.

Figure 11E:
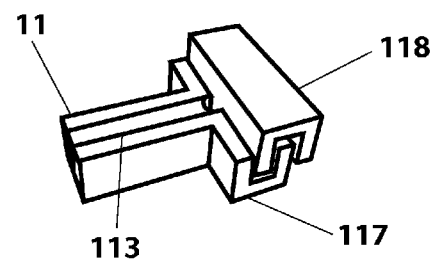
FIG. 11E is a perspective view of an alternate embodiment of the system which enables the flow of fluid from one open microfluidic channel to another in an approach that allows the building of open microfluidic networks.
Figure 11C:
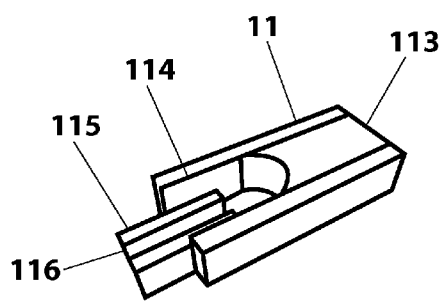
FIG. 11C is a perspective view of an open microfluidic network built inside a larger open microfluidic network, according to one embodiment.

FIGS. 11C-11D are perspective views of an embodiment which enables the flow of fluids from one open microfluidic channel to another in an approach that allows the building of open microfluidic networks that can be easily assembled and separated by standard open microfluidic components. In this method the open microfluidic channel 11 is ended at an extremity 114 which would stop the flow of fluid due to pinning. A second open microfluidic channel or part of a channel 115 is placed in close proximity to the channel 11 and fluid transfer from one channel to the other is enabled through the contact of the part of a channel 115 interior to the extremity 114. As fluid is flowing by capillary force along channel 11, it is brought into contact with the channel 115, which allows fluid 113 to flow from channel 11 into channel 116, enhanced by the contacting surface area of the channel or parts of a channel 115.

Figure 11F:
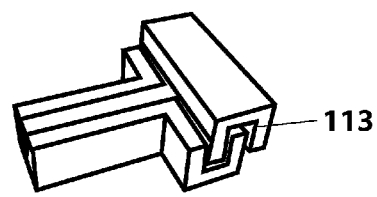
FIG. 11F is a perspective view of the embodiment of FIG. 11E showing fluid flow.

FIGS. 11E-11F are perspective views of an alternate embodiment which enables the flow of fluid 113 from one open microfluidic channel to another in an approach that allows the building of open microfluidic networks that can be easily assembled and separated by standard open microfluidic components. In this method the open microfluidic channel 11 terminates at an extremity 117 which would stop the flow of the fluid 113 due to pinning. This extremity 117 would have two openings positioned directly across from each other in the channel 11. An interior structure 118a second microfluidic channel is placed directly through these two openings within channel 11 and fluid transfer from one channel to the other is enabled through the contact of the part of a channel, which is an interior structure 118 to the extremity 117. As the fluid 113 flows by capillary force along channel 11, it is brought into contact with the interior structure 118, which allows fluid to flow from channel 11 into channel 119, enhanced by the depth of the interior structure 118 interior to the extremity 117.

Figure 12A:
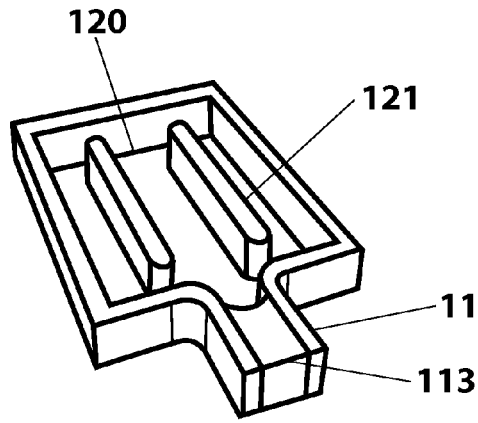
FIG. 12A is a perspective view of an alternative embodiment of the system facilitating the flow of fluids from one open microfluidic channel into a larger volume reservoir in an approach that allows the filling of an open microfluidic reservoir of variable volumes that is accessible from at least one opening.
Figure 12B:
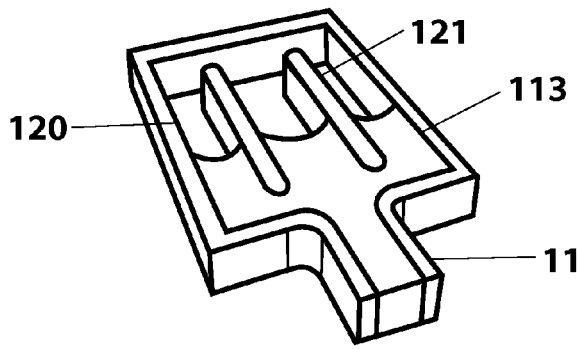
FIG. 12B is a perspective view of the embodiment of FIG. 12A showing fluid flow.
Figure 12C:
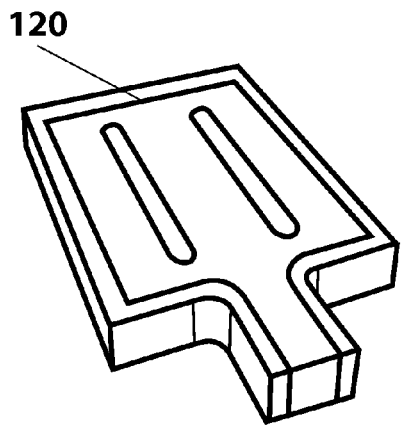
FIG. 12C is a perspective view of the embodiment of FIG. 12A, again showing fluid flow.

FIG. 12A-12C are perspective views of various alternative embodiments facilitating the flow of fluids from one open microfluidic channel into a larger volume reservoir in an approach that allows the filling of an open microfluidic reservoir of variable volumes that is accessible from at least one opening. In these embodiments, the open microfluidic channel 11 enters a reservoir 120 that contains fluid contact ridges 121 that enhance the surface area of the reservoir 120. These fluid contact ridges 121 may be spaced such that the fluid contact ridges 121 would allow the fluid 113 to transfer from the open microfluidic channel 11 into the reservoir 120 and capillary forces would maintain the fluid in the reservoir 120 enhanced by fluid contact ridge number and surface area (as designated by the fluid contact ridges 121).

Figure 13A:
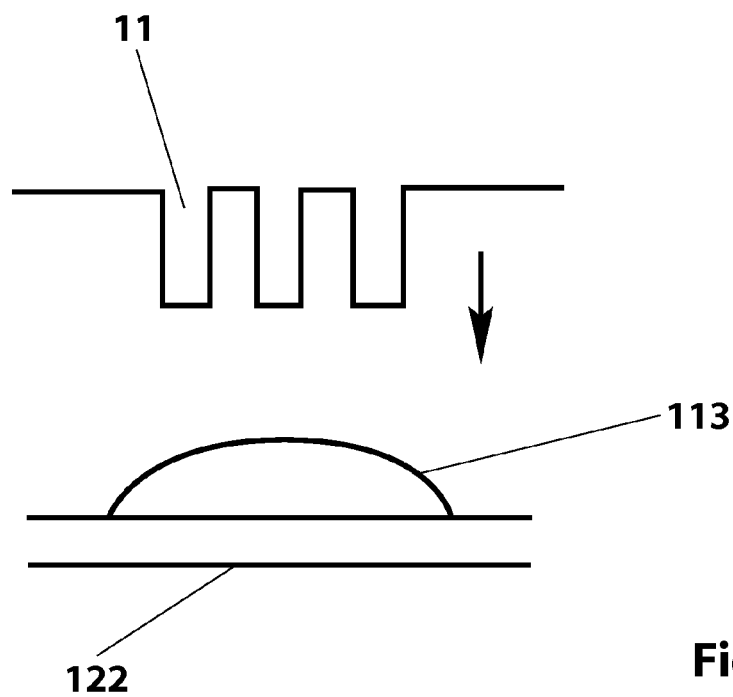
FIG. 13A is a side view of an exemplary embodiment of the system enabling the capture of excess fluid on a surface through open microfluidic channels to dry or remove liquids from a surface.
Figure 13B:
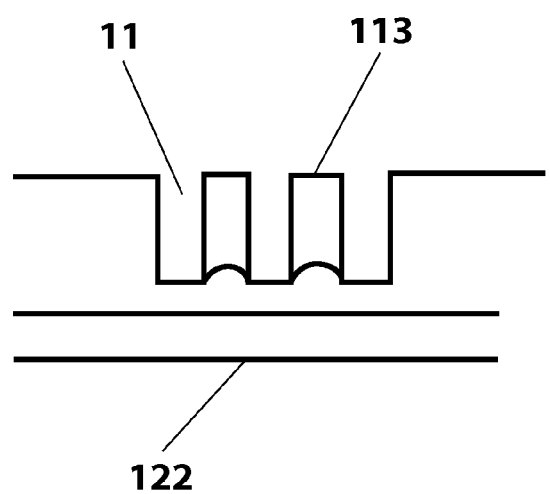
FIG. 13B is a side view of another exemplary embodiment of the system enabling the capture of excess fluid on a surface through open microfluidic channels to dry or remove liquids from a surface.

FIG. 13A-13B are a perspective views of a embodiments of a method enabling the capture of excess fluid 113 on a surface 122 through open microfluidic channels 123 to dry or remove liquids in a simple way from a surface 122. In this method the open microfluidic channels 123 come into close proximity with the surface 122 such that the fluid 113 on the surface 122 will come into contact with the channels 123 and be pulled into the channels 123 and away from the surface 122.

FIGS. 14A-14B are perspective views of various embodiments of a method enabling the application of a substance 124 to an open microfluidic channel 11 or reservoir 120 as a simple method to apply treatments to a contained fluid. This substance 124 may be dried or otherwise immobilized to a surface 125 that would comprise paper, plastic, rubber, or another material and would be placed on the channel 11 or reservoir 120 bottom. In this method the substance 124 would be transferred to the channel 11 or reservoir 120 when fluid enters the area, allowing the substance to dissolve into the fluid. In another embodiment, FIGS. 14BC and 14D depict the embodiments in which the substance 124 is dried or otherwise immobilized to a surface 125 that would comprise paper, plastic, rubber, or another material and would be placed on the top of the channel 11 or reservoir 120. In these embodiments, the substance 124 would be transferred to the channel 11 or reservoir 120 when fluid is already contained in the area when the surface 125 contacts the fluid within the channel 11 or reservoir 120.

Figure 15:
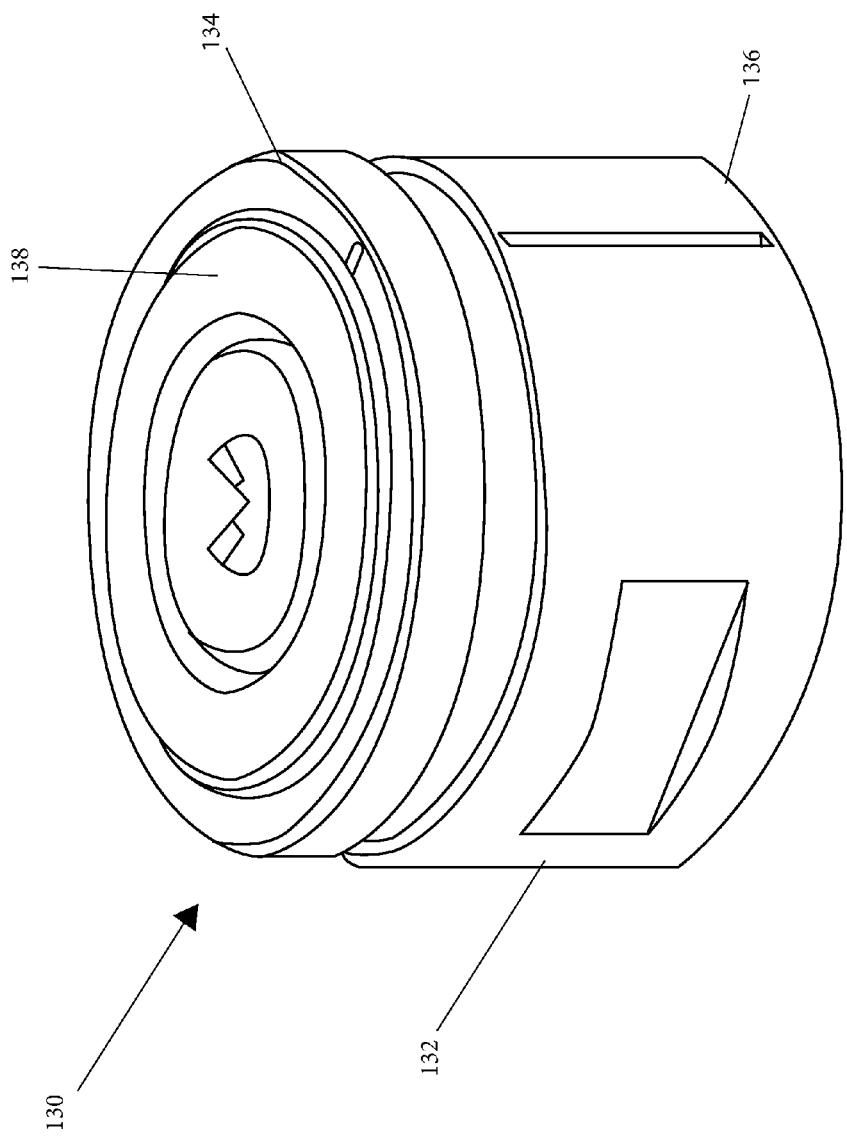
FIG. 15 is a perspective view of the handheld device, according to one embodiment.
Figure 16:
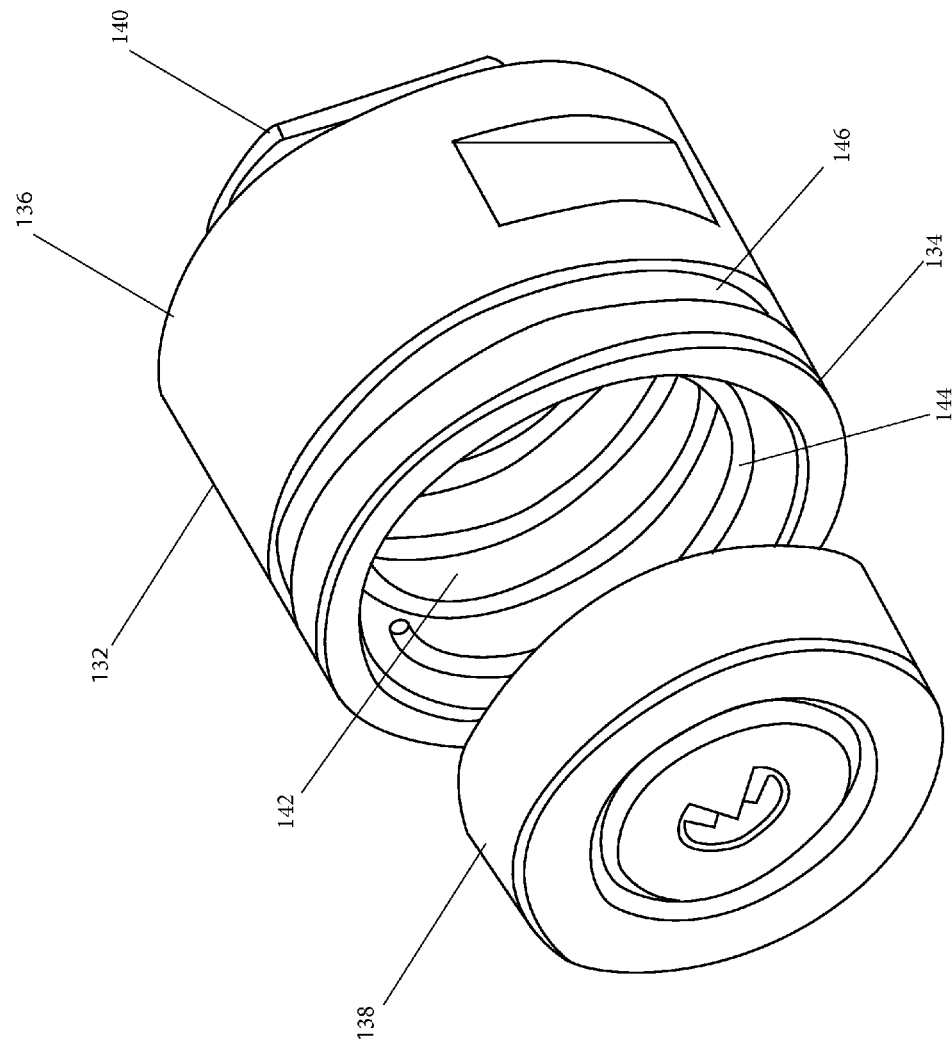
FIG. 16 is an exploded front view of the handheld device, according to one embodiment.

FIG. 15 is a perspective view of an exemplary embodiment of a handheld device 130. It is understood that various device and system embodiments disclosed herein, including the handheld device 130 of FIG. 15, can be used for a variety of medical procedures and tasks including, but not limited to, bodily fluid collection and analysis. For example, as shown in FIG. 15 in accordance with one embodiment, the handheld device 130 contains a body 132 with a proximal end 134 and distal end 136. A plunger 138 rests between the proximal end 134 and the distal end 136. According to one implementation, the body 132 defines a lumen 142 (as best shown in FIG. 16) disposed through the body 132, such that the body 132 in certain embodiments is considered a "hollow body" 132). The body 132 may be cylindrical in shape as illustrated in FIG. 15, however other shapes such as oval, square, triangular, and the like may be readily used as well. Further, the lumen 142 can also be cylindrical, oval, square, triangular, or any other known shape for a lumen. The plunger 138 is disposed in the lumen 142 between the proximal end 134 and the distal end 136 of the body 132, such that its displacement may be controlled by a user-imparted force. It is understood that the device embodiments disclosed herein can also be used with any other known system.

FIG. 16 is an exploded perspective view of an exemplary embodiment of the handheld device 130 on its side, in accordance with one implementation. The handheld device 130 contains the body 132 with the proximal end 134 and the distal end 136. The plunger 138 fits into the proximal end 134 of body 132, and a base 140 attaches to the distal end 136 of the body 132. The body 132 defines a lumen 142 extending longitudinally, in some implementations, from the distal end 136 to the proximal end 134. According to one aspect, the lumen 142 can also be known as a "vacuum creation space" 142. The body 132 also has a spring 144 and a membrane tethering area 146. To use the handheld device 130, a user places the handheld device 130 on a subject's skin, creating a seal. In an alternative embodiment, an adhesive is attached to the distal end 136 of the handheld device 130 to adhere the handheld device 130 to the subject's skin and create a seal.

In these exemplary embodiments, when a user actuates the handheld device 130 by imparting a force on the plunger 138, the plunger 138 is displaced towards the distal end 136 of the body 132 through the lumen 142. Once the plunger 138 reaches its full displacement, a mechanism for retracting the plunger 138 is triggered. In the embodiment shown in FIG. 16, the mechanism for retracting the plunger 138 is the spring 144. In an alternative embodiment, a membrane may be attached to the membrane tethering area 146, and the membrane may be used to retract the plunger 138. The mechanism for retracting the plunger 138 may be activated by the user's manual removal of the user-provided force on the plunger 138. In an alternative embodiment, when the user-imparted force pushes the plunger 138 past a trigger point, an internal mechanism in the handheld device 130 is triggered, activating the mechanism for retracting the plunger 138.

Figure 17:
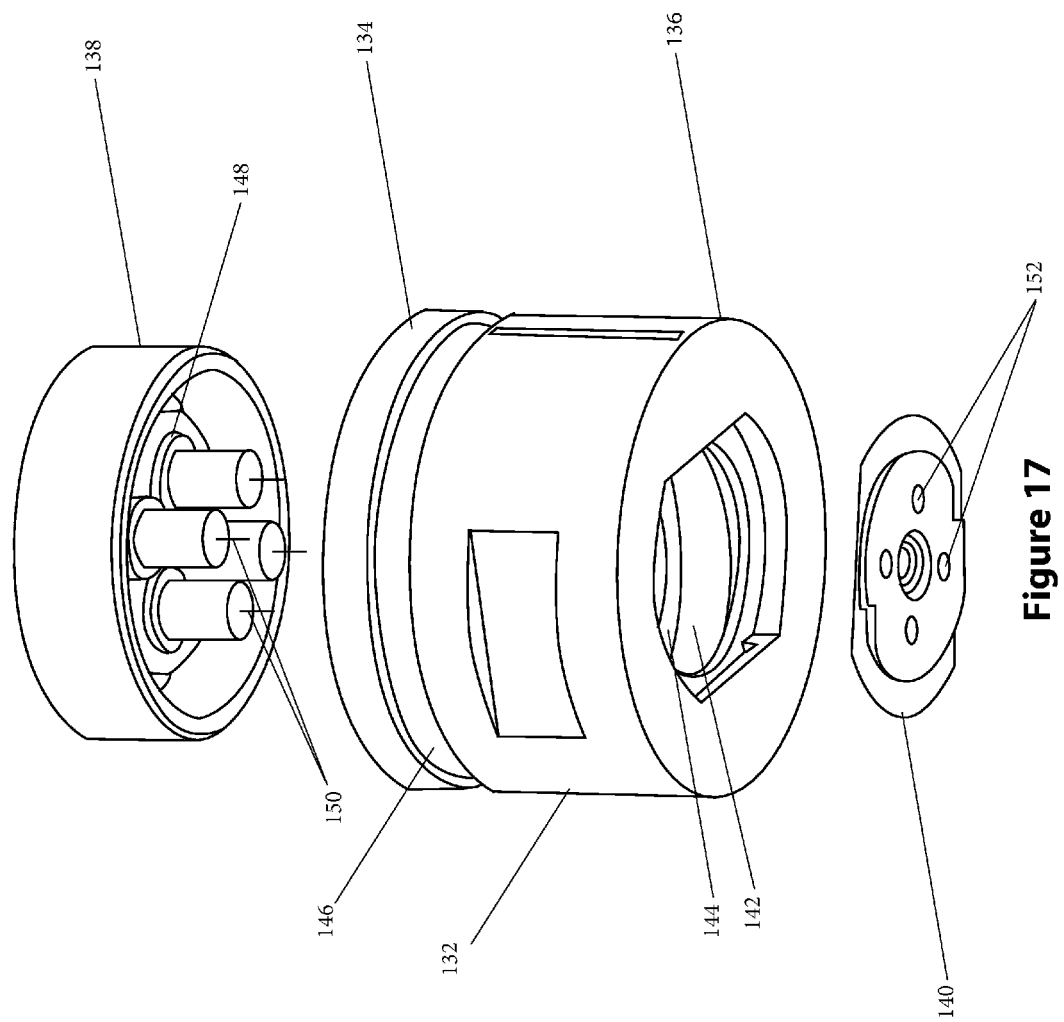
FIG. 17 is another exploded perspective view of the handheld device, according to one embodiment.

FIG. 17 is another exploded perspective view of an exemplary embodiment of the handheld device 130, in accordance with one implementation. The plunger 138 is configured to be inserted into the lumen 142 at the proximal end 134 of the body 132 and contains a face 148 and a plurality of needles 150. The plurality of needles 150 is fixed to the face 148. The base 140 attaches to the distal end 136 of the body 132 and contains a plurality of apertures 152 that are in fluid communication with the lumen 142 and match with the needles 150 on the plunger 138. The plurality of needles 150 may include needles having a gauge from 140 gauge to 40 gauge. In some embodiments, the needles are from 29 gauge to 40 gauge. In an alternative embodiment, the plurality of needles 150 may include a plurality of microneedles. In the embodiment shown in FIG. 17, the plurality of apertures 152 on the base 140 illustratively includes four apertures. In alternative embodiments, the plurality of apertures 152 may include from two to one hundred apertures. The plurality of needles 150 is aligned to be guided to pass through the plurality of apertures 152 when a user actuates the handheld device 130.

Figure 18:
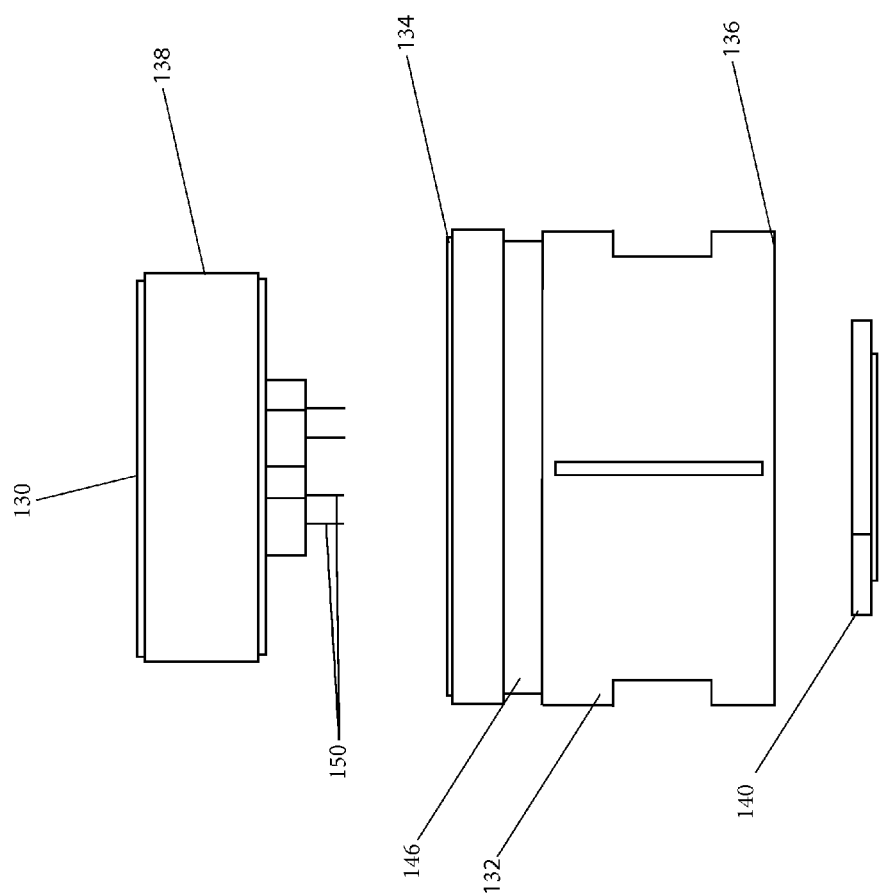
FIG. 18 is an exploded front view of the handheld device, according to one embodiment.
Figure 19:
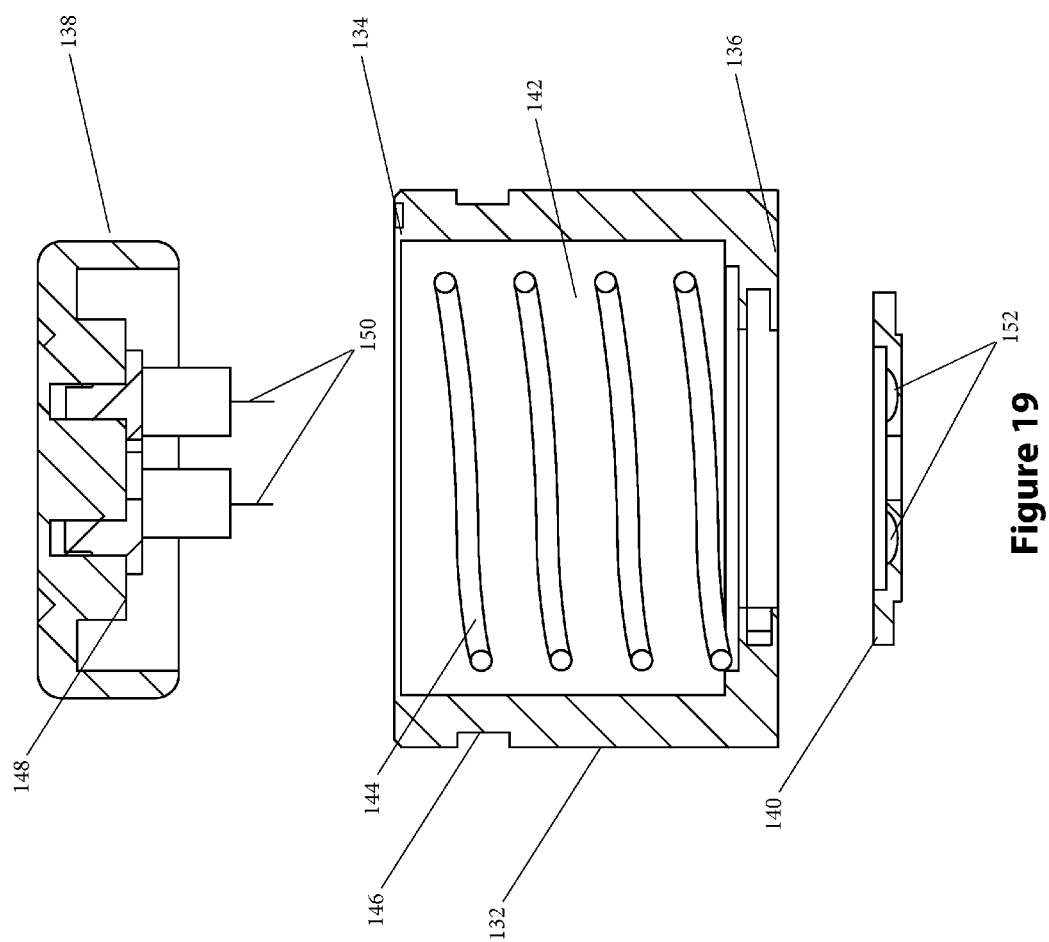
FIG. 19 is an exploded cross sectional front view of the handheld device, according to one embodiment.

FIG. 18 is an exploded front view of the handheld device 130, in accordance with one implementation, and MG. 19 is an exploded cross sectional front view of the handheld device 130, respectively, in accordance with one implementation. In these and other exemplary embodiments, each of the plurality of apertures 152 on the base 140 defines a fluid extraction site. The plurality of needles 150 is fixed to the face 148 of the plunger 138 and configured such that when a user actuates the handheld device 130, the plunger 138 is urged distally and the plurality of needles 150 is guided through the plurality of apertures 152 on the base 140, and at least one of the plurality of needles 150 penetrates the subject's skin to release bodily fluid. At least one of the plurality of needles 150 penetrate a subject's skin at a low velocity and as a result, not all of the plurality of needles 150 will necessarily penetrate the subject's skin. All of the plurality of needles 150 may penetrate the skin. However, even when less than all of the plurality of needles 150 penetrate a subject's skin, the handheld device 130 achieves high extraction reliability and is able to accommodate not all of the plurality of needles 150 penetrating the subject's skin, as there are multiple fluid extraction sites, or apertures 152 from which the plurality of needles 150 can draw bodily fluid.

By increasing the number of the plurality of needles 150, the handheld device 130 increases the probability of extracting a proper amount of bodily fluid. The configuration of the plurality of needles 150 thereby ensures bodily fluid extraction but without as much pain as is caused by a single, high velocity needle used in typical handheld fluid extraction devices or array devices. This approach also lowers the variability induced by the number of capillaries present at various locations on the subject's skin and differences or defects in the manufacturing of the plurality of needles 150. Additionally, the low velocity needle penetration allows a simple design for the handheld device 130, as low velocity needle penetration requires fewer mechanical parts than a typical high velocity device.

In one embodiment, bodily fluid extracted by the plurality of needles 150 may be blood. In another embodiment, bodily fluid extracted may be interstitial fluid. Once bodily fluid is extracted from the subject and begins to pool on the subject's skin, the mechanism for retracting the plunger 138 is activated. The spring 144 retracts the plunger 138 through the lumen 142 from the distal end 136 to the proximal end 134 of the body 132, removing the plurality of needles 150 from the subject's skin and creating a vacuum in the vacuum creation space in the lumen 142, which is the portion of the lumen 142 distal to the plunger 138. In an alternative embodiment, a membrane (not shown) may be attached to the membrane tethering area 146, and the membrane retracts the plunger 138 from the distal end 136 to the proximal end 134 of the body 132 through the lumen 142, removing the plurality of needles 150 from the subject's skin and creating a vacuum in the lumen 142 distal to the plunger 138. The vacuum created in the lumen 142 creates a vacuum at each of the fluid extraction sites, or apertures 152, thereby enhancing the pooling of bodily fluid on the subject's skin, optimizing fluid extraction from each puncture site where one of the plurality of needles 150 penetrates the subject's skin, and at the same time minimizing the size of each puncture site. The vacuum created may be from greater than 0 Pa to 75,000 Pa.

Figure 20:
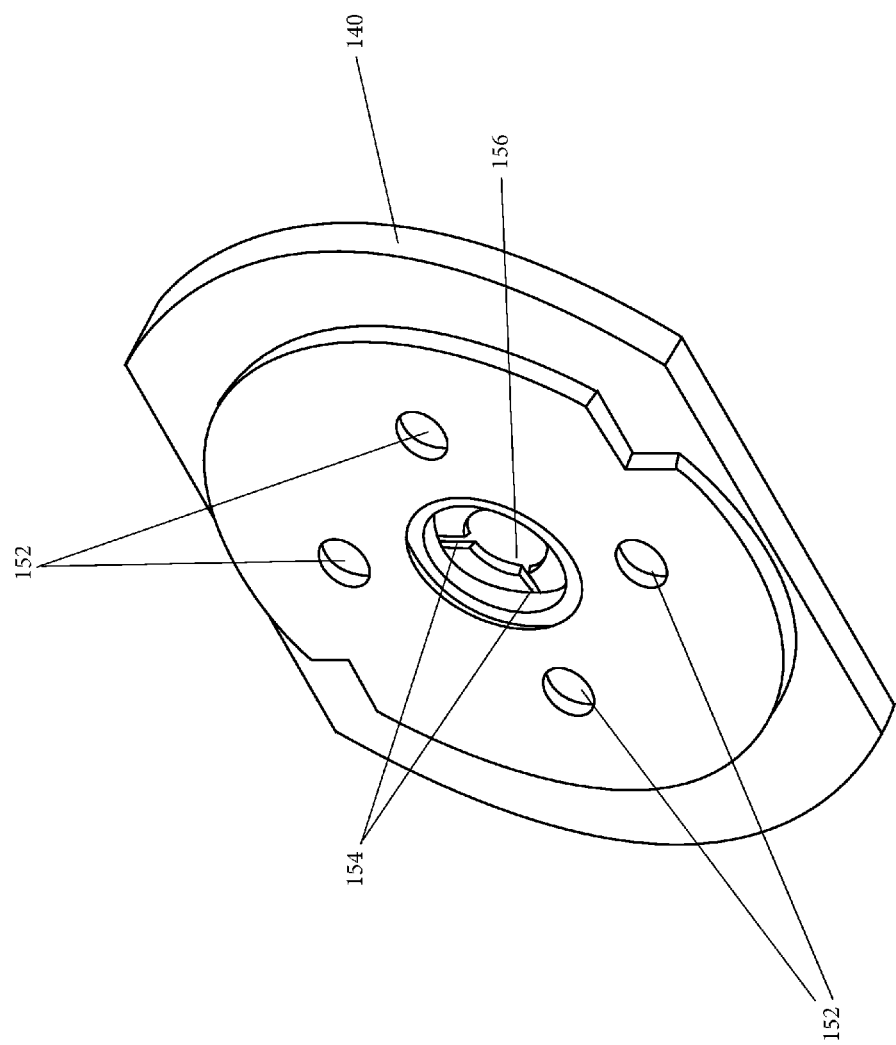
FIG. 20 is an isometric view of the bottom of the base of the handheld device, according to one embodiment.
Figure 21:
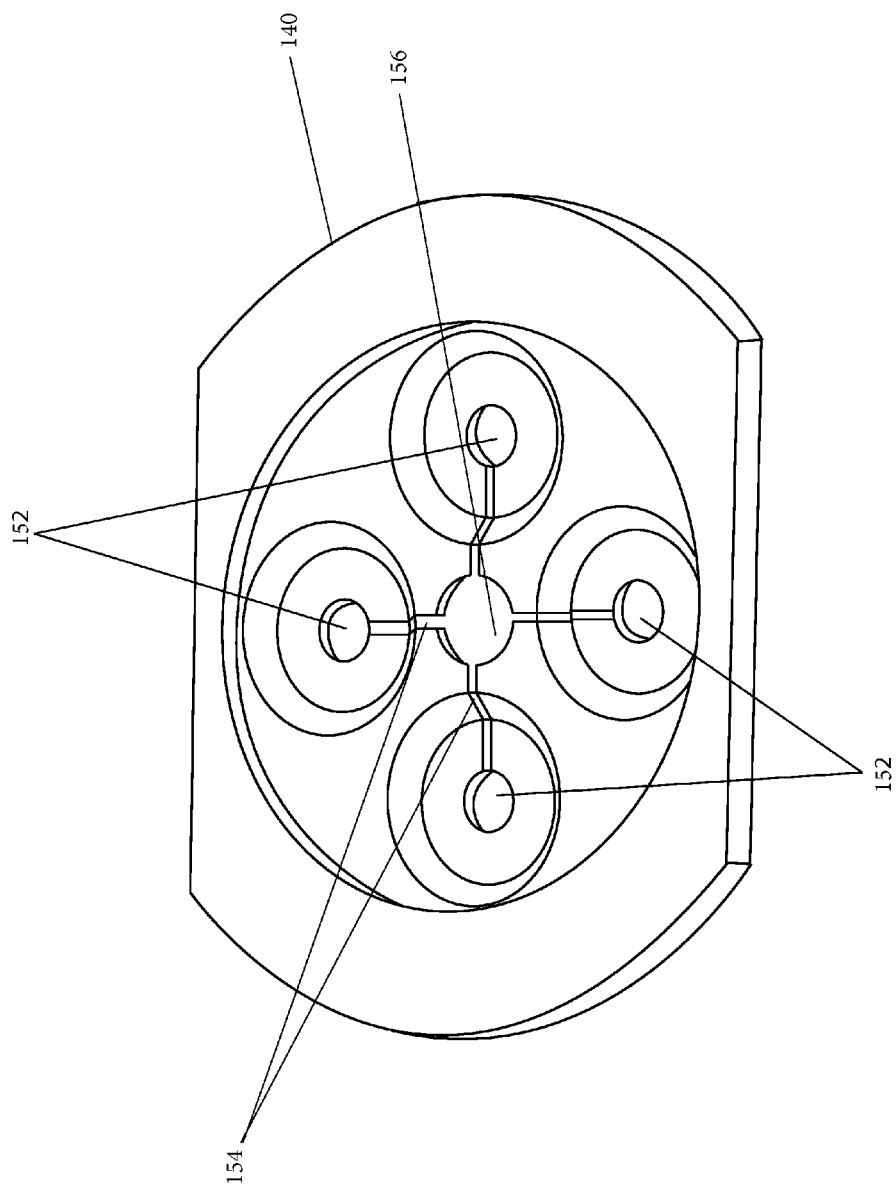
FIG. 21 is a perspective view of the top of the base of the handheld device, according to one embodiment.

FIG. 20 is an isometric view of the bottom of the base 140 of the handheld device 130 according to an exemplary embodiment. FIG. 21 is a perspective view of the top of the base 140 of the handheld device 130 according to an exemplary embodiment. In various embodiments, the base 140 contains the plurality of apertures 152, at least one sensing area 156, and a network of passages 154 in fluidic communication with the plurality of apertures 152 and the at least one sensing area 156, all of which are in fluidic communication with the lumen 142. In various embodiments, the needles (no shown) are able to slide through the apertures 152 so as to puncture the skin of the subject and cause bodily fluid to pool on the subject's skin. In the embodiments shown in FIG. 20 and FIG. 21, the network of passages 154 includes microfluidic channels that promote the pooled fluid to be directed toward the at least one sensing area 156 for collection and analysis. In exemplary embodiments, each of the plurality of apertures 152 is a part of such microfluidic channels. In alternative embodiments, the network of passages 154 may include tubes or paper channels.

When a user actuates the handheld device 130, resulting in bodily fluid pooling in at least one of the fluid extraction sites defined by the plurality of apertures 152 in the base 140, the network of passages 154 collects the bodily fluid pooling on the surface of the subject's skin from at least one of the fluid extraction sites. The network of passages 154 collects bodily fluid from any fluid extraction site in which fluid extraction by the plurality of needles 150 was successful. In the embodiment shown in FIG. 20 and FIG. 21, the network of passages 154 directs collected bodily fluid by capillary action to the at least one sensing area 156 on the base 140 for analysis. The at least one sensing area 156 collects the bodily fluid transported by the network of passages 154 and performs a sample preparation step. In one embodiment, the sample preparation step consists of filtration of erythrocytes of other constituents of the blood. In alternative embodiments, the sample preparation step may consist of bio-chemical labeling, cell-lysis, a bio-chemical reaction, or separation of the bodily fluid into different sub-components.

Figure 22:
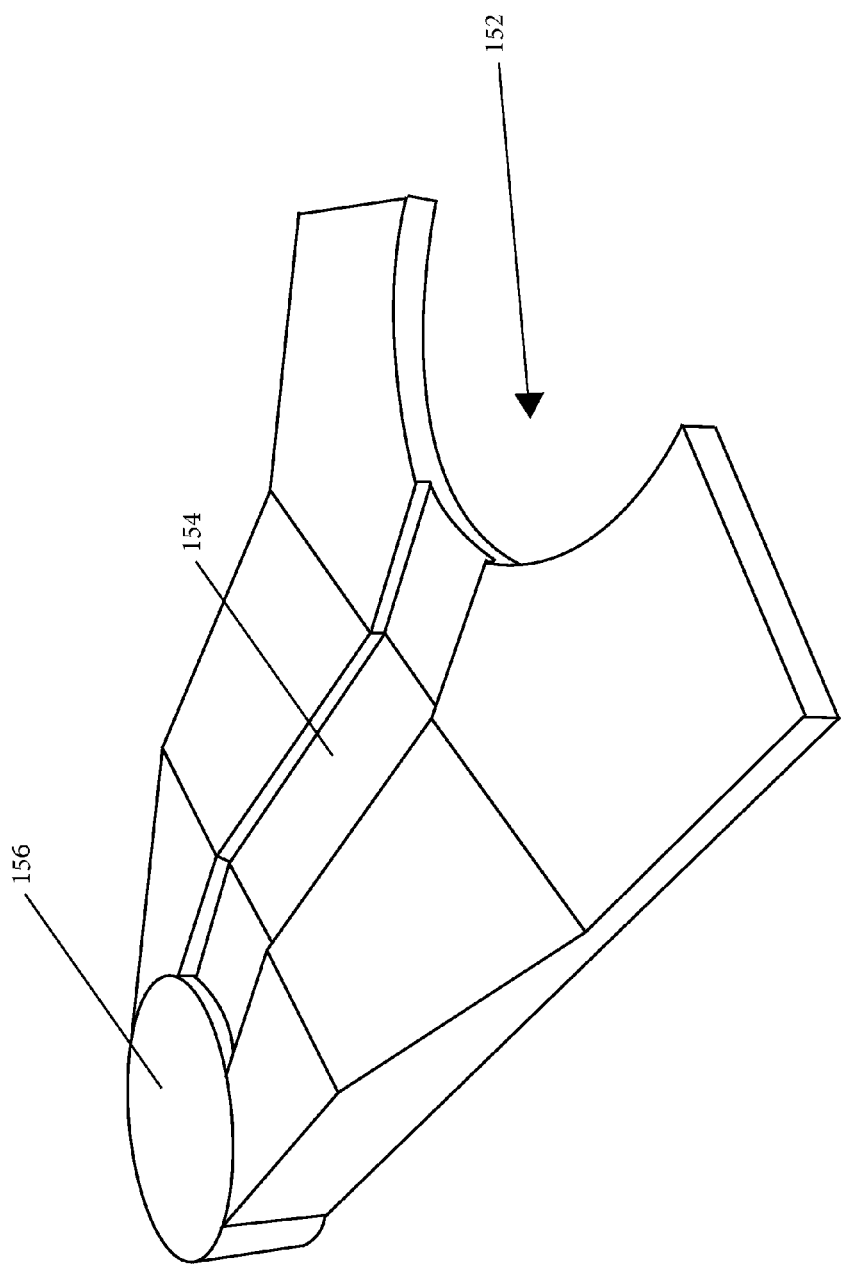
FIG. 22 is a perspective view of a portion of the top of the base of the handheld device, according to one embodiment.

FIG. 22 is a perspective view of a portion of the top of the base 140 of the handheld device 130 according to various embodiments. This portion of the top of the base 140 contains part of the network of passages 154, part of one of the plurality of apertures 152, defining part of a fluid extraction site, or aperture 152, and at least one sensing area 156. In this embodiment, a passage 154 of the network of passages 154 includes a U-shaped channel within a hydrophilic material such that the channel-fluid interface defining the wetted perimeter is larger than the liquid-air interface, defining the free perimeter. Bodily fluid is moved in a non-planar three-dimensional channel, allowing bodily fluid collection and analysis in at least one sensing area 156 to occur on different levels without increasing fabrication costs. Additionally, reliability is increased, as air bubbles do not cause fluid flow failure. In alternative embodiments, the geometry of each of the passages in the network of passages 154 may be varied to allow bodily fluid handling using one-way valves, passive fluid pumps, specific volume isolation for analysis, interfaces with a pad, and combinatorial flows.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology.

Although the disclosure has been described with reference to preferred embodiments, persons skilled in the art will recognize that changes may be made in form and detail without departing from the spirit and scope of the disclosed apparatus, systems and methods.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

Other embodiments are set forth in the following claims.

What is claimed is:

1. A medical device for collection of fluid from a patient comprising:
    a. a cylindrical housing having proximal and distal ends, the housing comprising defining a lumen;
    b. a plunger, the plunger disposed within the lumen and comprising a distal plunger face comprising a plurality of lancets;
    c. at least one fluid collection sites disposed defined within the distal housing end; and
    d. a microfluidic network disposed within the lumen and in fluidic communication with the at least one fluid collection sites, the microfluidic network comprising a first open channel comprising:
        i. a top portion comprising a first free surface defined by the top portion defining a first free perimeter; and
        ii. a first wetted surface defining a first wetted perimeter, wherein the first wetted surface contacts fluid flowing through the first open channel at a first contact angle,
    wherein the ratio of the first free perimeter to the first wetted perimeter is less than the cosine of the first contact angle, thereby enabling spontaneous capillary flow through the first open channel.

2. The device of claim 1, further comprising a second open channel.

3. The device of claim 2, wherein the medical device is configured to promote three-dimensional fluid flow by allowing fluidic travel in multiple planes relative to the body of the device.

4. The device of claim 2, wherein the medical device further comprises:
   a. a reservoir; and
   b. a plurality of apertures in fluidic communication with the first and second open channels,
   wherein the device is configured to promote spontaneous capillary flow of fluid from the plurality of apertures to the reservoir.

5. The device of claim 2, wherein the microfluidic network further comprises:
   a. a first plane comprising a first plane axis; and
   b. a second plane comprising a second plane axis,
   wherein the first plane axis and second plane axis are not co-axial.

6. The fluid collection system of claim 5, further comprising a reservoir in fluidic communication with the microfluidic network wherein the first plane axis is disposed adjacent to the collection site and the second plane axis is disposed between the first axis and the reservoir.

7. The device of claim 2, further comprising a reservoir in fluidic communication with the microfluidic network, wherein:
   a. the at least one fluid collection site comprises a first aperture and a second aperture,
   b. the first aperture is in fluidic communication with the first open channel; and
   c. the second aperture is in fluidic communication with the second open channel.

8. The device of claim 2, wherein the second open channel comprises a second cross-section comprising:
   a. a wetted surface, wherein the wetted surface defines a wetted perimeter and contacts fluid flowing through the channel at a contact angle; and
   b. a free interface comprising an open air-liquid interface which defines a free perimeter,
   wherein the second channel is in fluidic communication with the first channel so as to enable fluid flow between the channels, and
   further wherein the second channel has a second cross-section with a ratio of a cross-sectional length of a free interface to a cross-sectional length of a wetted surface that is smaller than the ratio of the first cross-section.

9. The device of claim 2, wherein the first open channel is configured to contact fluid pooling on the surface of the skin by way of the extraction collection site, thereby drawing the fluid into the first channel.

* * * * *